United States Patent [19]
Cash, Jr. et al.

[11] Patent Number: 6,125,295
[45] Date of Patent: Sep. 26, 2000

[54] PHARMACEUTICALLY ENHANCED LOW-ENERGY RADIOSURGERY

[76] Inventors: Webster C. Cash, Jr., 4323 N. 30th St., Boulder, Colo. 80301; Michael D. Weil, 2409 Bitterroot La., Golden, Colo. 80401

[21] Appl. No.: 09/140,981

[22] Filed: Aug. 27, 1998

Related U.S. Application Data

[60] Provisional application No. 60/057,106, Aug. 27, 1997.

[51] Int. Cl.[7] .......................................................... A61B 6/00
[52] U.S. Cl. ............................................... 600/431; 378/65
[58] Field of Search ..................................... 600/431, 425, 600/427; 378/62–65; 250/370.08, 370.09, 375

[56] References Cited

U.S. PATENT DOCUMENTS

| | | | |
|---|---|---|---|
| 4,598,415 | 7/1986 | Luccio et al. | 378/119 |
| 5,008,907 | 4/1991 | Norman et al. | |
| 5,604,782 | 2/1997 | Cash, Jr. | |
| 5,919,135 | 7/1999 | Lemelson | 600/407 |

OTHER PUBLICATIONS

Iwamoto et al., "Radiation dose enhancement therapy with iodine in rabbit VX–2 brain tumors," Radiother. Oncol. 8:161, 1987,Elsevier.

Iwamoto et al., "The CT scanner as a therapy machine," Radiother. Oncol. 19:337, 1990, Elsevier.

Santos Mello et al., "Radiation dose enhancement in tumors with iodine," Medical Physics 10:75, 1983, Am. Asoc. Phys. Med.

Norman et al., "Iodinated contrast agents for brain tumor localization and radiation dose enhancement," Invest. Radiol. 26:S120, 1991.

Callisen et al., "Absorbed dose in the presence of contrast agents during pediatric cardiac catheterization," Medical Physics 8:504.

Dawson et al., "Iodinated contrast agents as 'radiosensitisers'," Brit.J.Radiol. 60:201, 1987.

Fairchild et al., "Radiation enhancement with iodinated deoxyuridine," Invest. Radiol. 17:407, 1982.

Hadnagy et al., "Enhancedyield of chromosomal aberrations in human peripheral lymphocytes in vitro using contrast media in; Nov./Dec. 1979 X–irradiation," Mutation Res. 104:249, 1982, Elsevier.

Cochran et al., "Chromosome damage from nonionic contrast media," Invest. Radio. 29:S206, 1994, J.B. Lippincott.

Cohen et al., "Contrast–enhanced magnetic resonance imaging estimation of altered capillary permeability in experimental mammary carcinomas after x–irradiation," Invest. Radiol. 29:970, 1994, J. B. Lippincott.

Norman et al., "Effects of age, sex and diagnostic X–rays on chromosome damage," Int. J. Radiat. Biol. 46:317, 1984.

Adams et al., "Effect of radiation and contrast media on chromosomes," Radiology 124:823, 1977.

Cochran et al., "Induction of micronuclei in lymphocytes of patients undergoing excretory urography with Ioversol," Invest. Radiol. 29:210, 1994, J. B. Lippincott.

Matsubara et al., "Effects of contrast medium on radiation–induced chromosome aberations," Diag. Radiol. 144:295, 1982.

Saigusa et al., "Induction of chromosome aberrations by monochromatic X–rays with resonance energy of phosphorus K–shell absorption edge," Int. J. Radiat. Biol. 61:785, 1992, Taylor & Francis Ltd.

Weber et al., "Biological dosimetry after extensive diagnostic X–ray exposure," Health Physics 68:266, 1995.

Cochran et al., "Cytogenetic effects of contrast material in patients undergoing excretory urography," Radiology 136:43, 1980.

*Primary Examiner*—Brian L. Casler
*Attorney, Agent, or Firm*—Dorr, Carson, Sloan & Birney, P.C.

[57] ABSTRACT

Contrast agents developed specifically for x-ray diagnostics provide dose-enhanced radiotherapy and radiosurgery. The presence of heavy elements from these contrast agents, even small quantities, leads to a major dose increase in target tissue. When combined with in vivo calibration of the amount of contrast agent, the procedure is quick, accurate, and safe. The technique can also be used in combination with other techniques, such as focused x-rays, to achieve further enhancement of therapeutic ratio. Through optimization of the equipment it is possible to achieve very large ratios of dose in target to dose in healthy tissue up to 10:1.

35 Claims, 13 Drawing Sheets

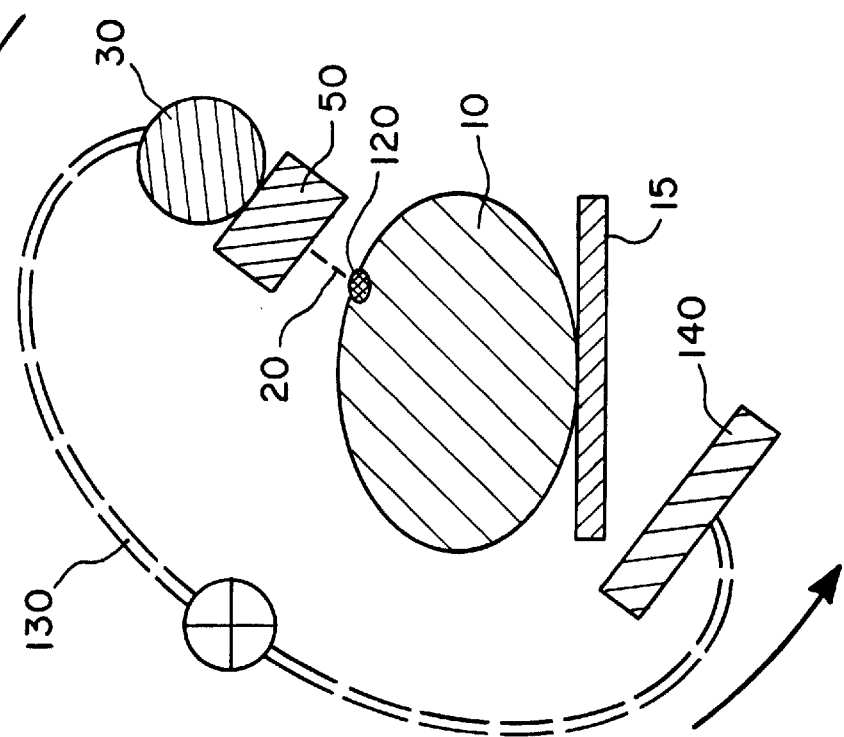
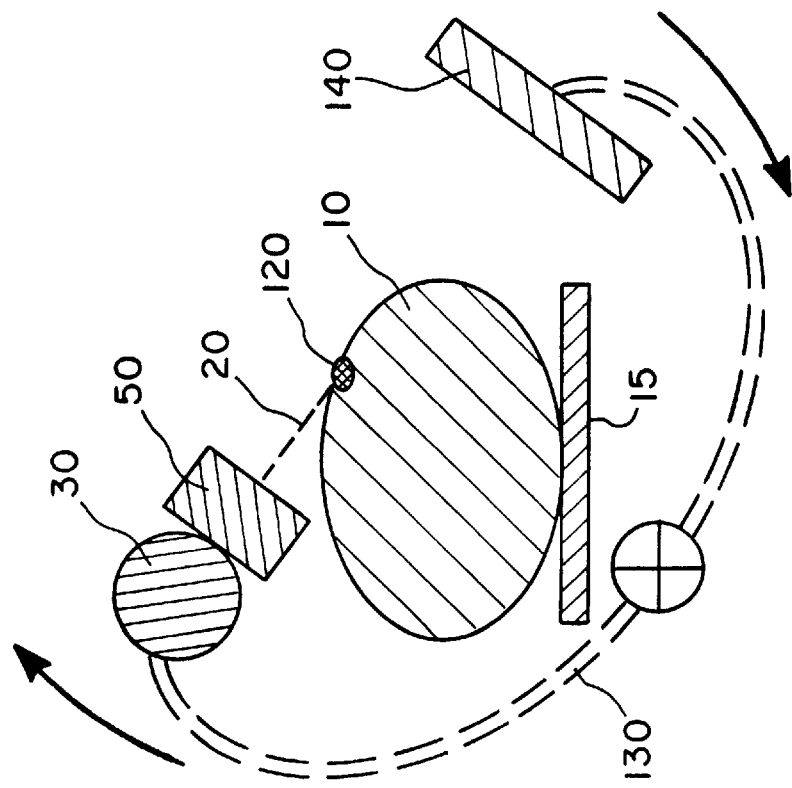

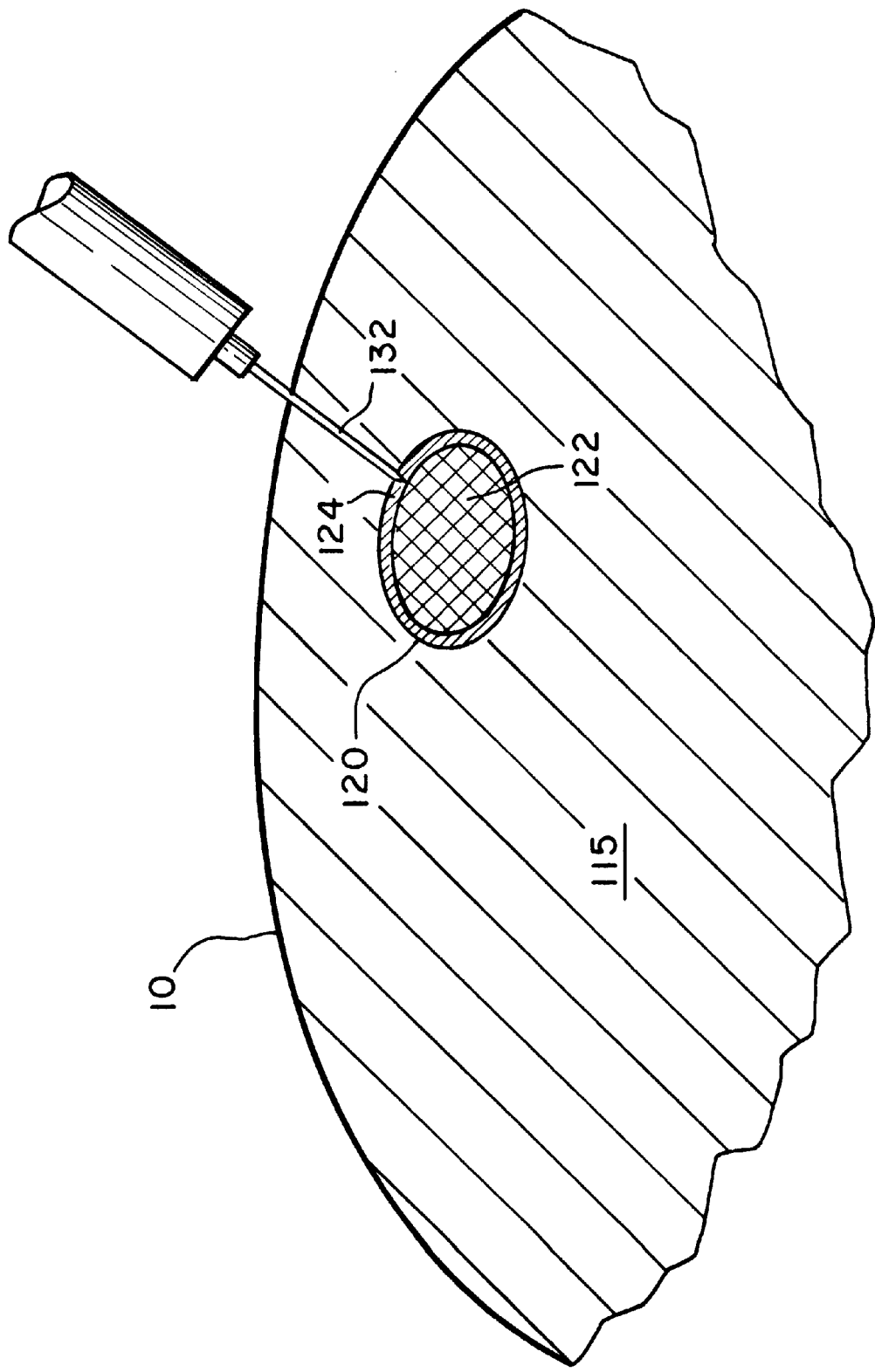

PHARMACEUTICALLY ENHANCED LOW-ENERGY RADIOSURGERY

RELATED APPLICATIONS

This application claims the benefit of U.S. Provisional Application No. 60/057,106, filed Aug. 27, 1997.

FIELD OF THE INVENTION

The present invention relates to the fields of x-ray therapy and x-ray surgery. More specifically, devices and enhanced methods for performing such therapeutic techniques, comprising the use of pharmaceutical contrast agents, are provided.

BACKGROUND OF THE INVENTION

Since early in the twentieth century it has been recognized that the ionizing properties of x-rays allow them to be used for therapeutic and diagnostic purposes. However, treatment of tumors with x-rays is difficult because about the same x-ray dose is required to kill the cancerous cells as kills healthy cells. Therefore, techniques for concentrating the x-ray dose in the target area, with minimum dose to surrounding healthy tissue, are of basic importance in radiotherapy and radiosurgery.

An example of radiotherapy is illustrated in FIG. 1. Radiotherapy consists of bathing large volumes of the body 10 in direct radiation 20 generated from a conventional therapy x-ray source 30. Usually performed at 1 MeV or more, the goal is to damage both healthy and diseased cells. The healthy cells are better able to repair the damage and remain viable while the diseased cells die.

In recent years, photons with energy in excess of 1 MeV have been preferred for therapeutic purposes over the more traditional medical x-rays in the 50 to 100 keV band. This is because of several factors. First, the beam intensity drops less quickly as it passes through the body, yielding a more uniform dose at the target site. Second, the primary photoelectrons (which cause tissue damage) are created by Compton scattering of the high-energy photons and penetrate inward from the site of the interaction. This leads to low dose deposition at the skin, and a buildup effect inward. Third, because the beam absorption is dependent only on the density of the tissue, and not upon the composition, there is little interaction with bones.

In the last fifteen years, as computed tomography (CT) and magnetic resonance imaging (MRI) have improved imaging of the body, a new technique, known as radiosurgery, has been developed. Radiosurgery is illustrated in FIG. 2. Radiosurgery targets a specific part of the body, such as the head 12. By moving the x-ray source 30 through an arc as shown by the arrows 40, with the isocenter at the hub of the arc 40, the diseased tissue is given a higher dose than the healthy tissue. To achieve a lethal x-ray dose deep inside the body, the x-ray beam is brought to bear on the target tumor from a variety of directions, spreading the beam across as much healthy tissue as possible, but always remaining aimed at the target. This is done by creating dozens of narrow beams from radioactive decay (as in the case of the gamma knife) or by scanning an x-ray source across a series of arcs in the case of a linear accelerator (LINAC). Both techniques are effective and in general practice. However, even with these radiosurgical techniques, collateral damage to nearby tissue remains a major problem because the x-ray beams spread to the side and overshoot the target.

Contrast agents are currently used to enhance the x-ray visibility of soft tissue structures. The higher cross section that the heavy elements present to the x-rays used in medical applications allows this technique to be successful. This x-ray dose enhancement caused by the contrast agents has been viewed as a detrimental side effect of diagnostic imaging in the past because it causes cellular, particularly DNA, damage. Such concerns are discussed in the literature, mostly relating to angiography or excretory urography, two procedures that deliver exceptionally high diagnostic doses to the patient, as discussed by Callisen et al., Cochran et al., and Weber et al.

From concerns related to cell damage caused by the use of high doses of contrast agents came the idea that the damaging effects on cells could be used to improve radiotherapy. Several papers have discussed the use of contrast agents to enhance the effect of x-rays for tumor treatment and have demonstrated that enhancement works in several model systems. Hadnagy et al. showed that contrast agent alone or contrast agent combined with x-rays increased radiation-induced chromosomal aberrations in blood cells. The amount of aberration was dependent on iodine concentration. Fairchild et al. relates to theoretical considerations of the use of iodinated deoxyuridine as an enhancing agent for treating tumors. Santos Mello et al. refers to considerations and results relating to the therapeutic advantages of loading tumors in mice, particularly brain tumors, with iodine and treating them with low-energy photons. They achieved a dose enhancement of up to 3 in lymphocytes. Iwamoto et al. relates to use of low-energy x-rays and iodine to treat brain tumors in rabbits. They found a dose enhancement of about 30% by using the combination. Dawson et al. relates to treating cells in vitro with various concentrations of iodine. They found radiation enhancement of cell damage with an iodine concentration of 50 mg/ml. Cochran and Norman relates to findings of chromosome damage in patients subjected to nonionic contrast media. Iwamoto et al. (see also U.S. Pat. No. 5,008,907) discusses the use of a CT scanner and collimator, together with contrast agent, to treat brain tumors. In this report, the dose enhancement was determined to be about 50%. Cohen et al. relates to use of Gd-DTPA contrast agent to detect changes in microvascular characteristics in rats implanted with a tumor. Norman et al. relates to use of iodinated contrast agent together with x-rays for treating brain tumors. They also suggest using gadolinium as a contrast agent.

None of these references proposes a device specifically designed to make maximum use of the contrast agent to enhance x-ray therapy or x-ray surgery or specific methods therefor.

None of these references discusses methods to precisely calibrate the amount of contrast agent desired in a tumor nor methods to accurately deliver the amount of contrast agent necessary to produce a radiation dose enhancement of greater than 2:1 in the tumor over the normal tissues. None of these references discusses methods of treating only the surface of the tumor to destroy the tumor vasculature and also maintain a safe dose of radiation to the normal tissues.

SUMMARY OF THE INVENTION

We have discovered that increased enhancement in the local x-ray dose to a target tumor can be created with the correct combination of x-rays and contrast agents. Contrast agents which comprise a heavy element, for example, iodine, gadolinium, or gold, are introduced into the patient either by direct injection or intravenously.

A typical contrast agent comprises a compound that contains a large percentage of a heavy element from the upper half of the periodic table, such as iodine, gadolinium, or gold. For x-ray diagnostics, the most common heavy element used is iodine. At diagnostic energies, typically about 18 to about 80 keV, the absorption cross section of iodine is much higher than that of the elements that form most human tissue. Thus, even in relatively small amounts, iodine can add significantly to the absorption of x-ray radiation.

A preferred method of the present invention for treatment of a tumor (or other target) comprises the following steps. First, the tumor is visualized by ultrasonography or computed tomography (CT), and contrast agent is delivered into the tumor, or into a surface portion of the tumor, preferably by intravenous or direct injection. Second, the amount of contrast agent in the tumor is calibrated. Third, the first two steps are iterated until a desired amount of contrast agent is achieved as uniformly as possible throughout the tumor or in the surface portion only of the tumor, in order to provide a desired amount of x-ray dose enhancement. Fourth, the tumor is irradiated by a low-energy, orthovoltage x-ray source before the contrast agent leaks from the tumor. We have discovered that with proper calibration as described herein, in most cases the tumor will show a strong to complete response within four weeks. Adjacent body tissues are completely unharmed.

In another preferred embodiment, the method for injecting the tumor includes the deliberate injection of only a surface portion of the tumor in cases where the tumor mass is too large to be filled in toto. Injection of the surface portion of large tumors permits delivery of higher doses of radiation to this area of the tumor than is possible with conventional or previously described techniques. It is believed that this method destroys the blood supply to the tumor and its growing periphery only. Therefore, we kill the cancer more efficiently than by conventional techniques that deliver a higher radiation dose to the center of the mass.

Although many tumors are small enough and soft enough to inject directly with contrast agents, we have found that this method will not work well for large or hard tumors. In the case of a tumor that is too big or too fibrotic to fully inject with enough contrast agent, the above-noted technique involving injection of the surface portion is used for treatment. Only the outer regions of the mass are injected and subsequently irradiated. The entire periphery or corona of the tumor is injected. These injections can be directed visually or by ultrasonography or CT. The depth of the injection may include up to about 20% to about 30% of the radius of the tumor. For example, in a tumor having a radius of 2 cm, the injected surface portion would extend up to 0.5 cm deep as measured from the circumference. After injection, the amount of the contrast agent is calibrated. The subsequent deposition of high doses of radiation to the entire sphere of tissue surrounding the tumor encases it in a shell lacking any vascular support.

In another embodiment of the present invention, contrast agent is intravenously injected. The contrast agent then spreads through the vascular system and, under normal conditions, is generally confined to that route. However, at the site of a tumor the vasculature is leaky. This allows the contrast agent to spread into the tissue of the tumor, where it accumulates to higher concentrations than in surrounding tissue. The amount of contrast agent in these regions of accumulation within the tumor is calibrated using diagnostic equipment. The percentage of iodine achieved in the tumor is often too low to achieve a sufficient therapeutic amount for a complete response, but when focused beams are used, highly advantageous results are achieved. Another use of intravenous delivery is when the blood vessels themselves are targeted (e.g., vascular malformations or pathology), since the therapeutic ratio of contrast agent in the blood can be very high, killing blood vessels, but not tissue.

Injections of tumors within the body are performed under the guidance of ultrasonography or CT visualization. Injections via ultrasound are performed in real-time and involve multiple needle placements to cover the volume. The needles are arranged to cover the lesion in a fashion that is analogous to the placement of sources for brachytherapy. However, once the injections are completed the needles are removed. Injections under CT guidance are similar, but the operator leaves the room between injections so as not to be exposed to radiation. Following the definition of the volume to be treated with the above methods, the amount of contrast agent is calibrated and the injections are repeated until high concentration is achieved. The amount of the contrast agent is calibrated from the digital output of orthogonal fluoroscopic or CT views of the lesions post-injection. We have discovered that by using such contrast agents, preferably with optically focused x-rays, for example, those produced according to U.S. Pat. No. 5,604,782, or various other methods of focusing x-rays as are known in the art, the therapeutic ability of the x-rays, particularly for treating tumors, is greatly enhanced.

Thus, the present invention comprises a method for treating tumors by pharmaceutically enhanced radiosurgery with focused x-rays beams that includes the steps of injecting a contrast agent either intravenously into the patient or directly into the tumor and then calibrating the amount of contrast agent within the tumor in order to determine the x-ray dose enhancement that exists in the tumor compared with the surrounding tissue, which contains less or no contrast agent. The calibration of the amount of contrast agent within the tumor is performed by using at least two equations. The first equation measures x-ray dose enhancement de on the basis of the weight percent p of contrast agent within the tumor, that is, by de=1+1.3 p. The second equation measures x-ray dose enhancement de on the basis of the Hounsfield number H for the contrast agent, that is, by de=1+0.0025 H. The Hounsfield number H is determined by placing the contrast agent-injected tumor in a CT scanner and measuring the Hounsfield number H directly off the display screen of the scanner. The injection of the contrast agent and the calibration of the amount of contrast agent to determine x-ray dose enhancement in the tumor are repeated until the desired amount of dose enhancement is achieved, from about 2:1 to about 10:1 compared with the dose in normal tissue. The tumor is then irradiated with a focused x-ray beam having an energy level of about 40 keV to about 80 keV. The x-ray beam is focused by a mirror array as described hereinbelow.

These and other advantages, features, and objects of the present invention will be more readily understood in view of the following detailed description and the drawings.

BRIEF DESCRIPTION OF THE DRAWINGS

FIGS. 16A and 16B show imaging of the injected contrast agent by fluoroscopy using orthogonal fields and digital readouts for calibration.

FIG. 17 demonstrates injection of a surface portion of a tumor with contrast agent.

DETAILED DESCRIPTION OF THE INVENTION

Figure 1:
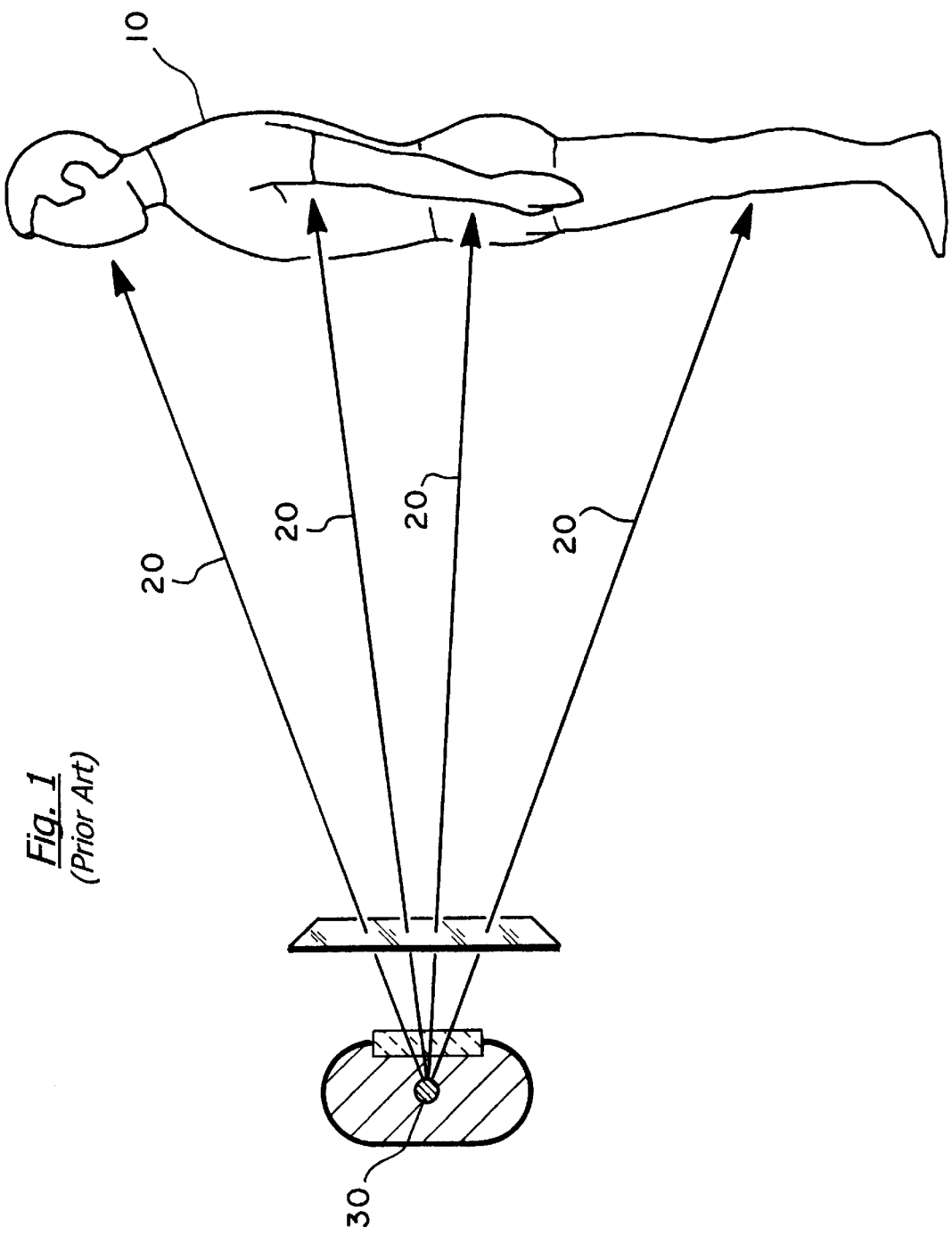
FIG. 1 is a view of prior art radiotherapy.
Figure 2:
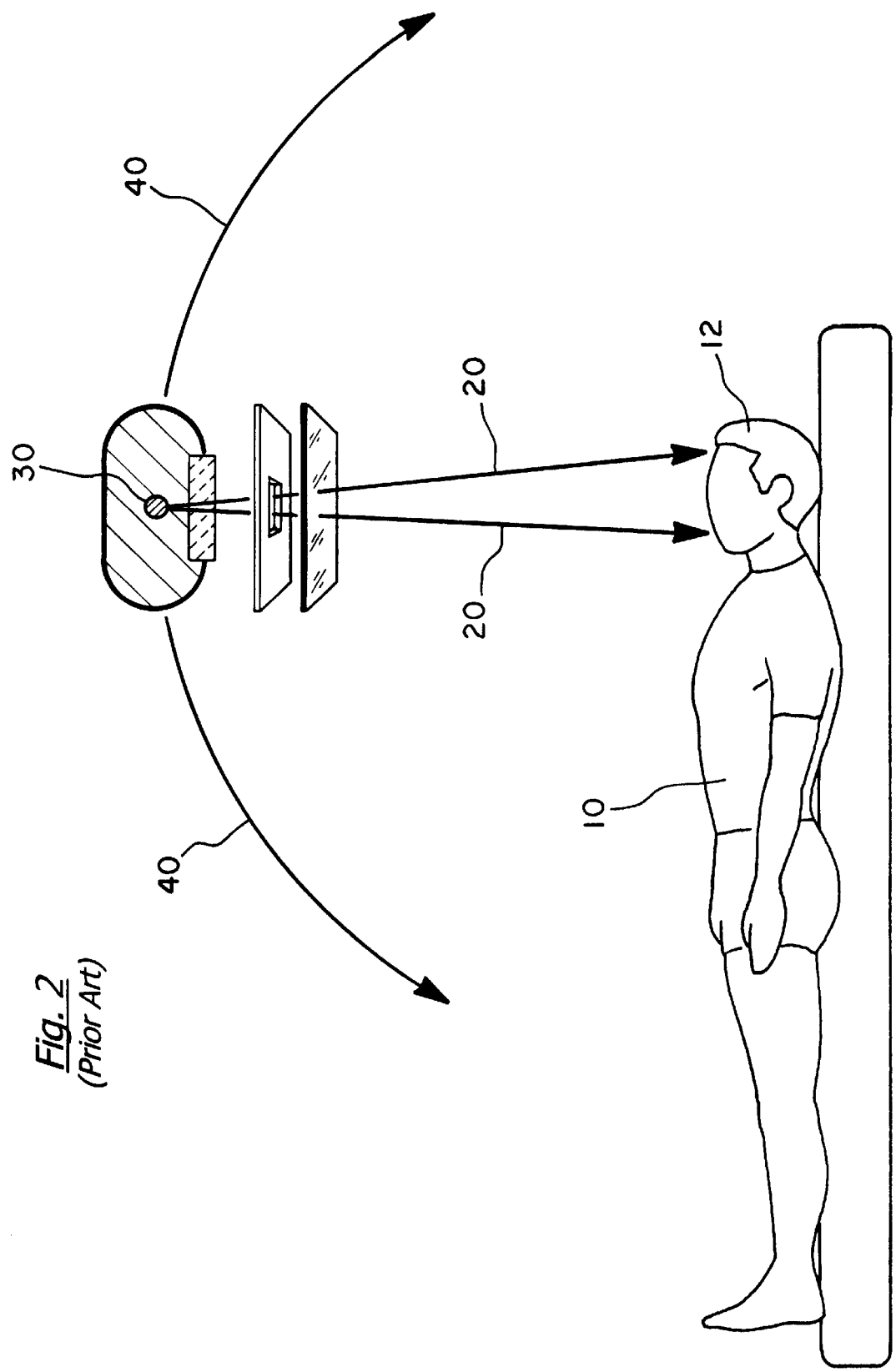
FIG. 2 is a view of prior art radiosurgery.

High-energy radiation is used in both radiotherapy and radiosurgery. As used herein, "radiotherapy" refers to bathing the patient's entire body in radiation (see FIG. 1). Tumor cells generally have a harder time recovering from radiation damage than do normal cells, and this gives the patient an advantage in the fight against the tumor. Typically, radiotherapy slows growth of cancer as opposed to curing it. As used herein, "radiosurgery" refers to use of beams of high-energy radiation designed to create a high dose in some chosen target within the body, for example, a tumor. Traditionally this is accomplished where beams intersect in the target, instead of in the healthy tissue (see FIG. 2).

When an x-ray encounters an atom, it interacts through one of three mechanisms: photoelectric absorption, elastic scattering, or Compton scattering. The relative probability of each interaction is a well-known function of the x-ray photon energy. Photoelectric absorption dominates at low energy and Compton scattering at higher energies. All three kinds of events are included in the cross section for diagnostics, as they remove photons from the primary x-ray beam. Elastic scattering is thus a significant contributor to diagnostics. However, during elastic scattering, no significant energy is transferred out of the photon as it changes direction. As a result, elastic scattering creates no ionization events in the body and has no ability to kill targeted cells.

Compton scattering is similar to elastic scattering, but the photon interacts with an individual electron and transfers a significant fraction of its energy to the electron. The Compton equation:

$$\lambda_f - \lambda_i = \lambda_c (1 - \cos\theta)$$

shows that the wavelength of the scattered photon is about 0.024 Å greater than before scattering. At 51 keV, this represents a 10% loss of energy to the photon. Thus, the scattered photon retains 90% of its energy and keeps traveling through the body. Only 10% of the energy is available for therapeutic effect.

The photoelectric effect is the most efficient for conversion of x-ray energy to ionization in the body. First, all the energy of the photon in excess of the K-edge energy is deposited in the primary photoelectron and thus causes ionization in the body. Second, the K-edge energy remaining in the atom is released through the emission of either a fluorescent x-ray or an Auger electron. If it is released through an Auger electron, then all the K-edge energy is contained in this second electron and causes tissue damage. If the event is fluorescent, the photon will be of lower energy than the original, and often cannot travel far. Overall, the photoelectric effect can create much more damage to tissue than will the Compton effect or elastic scattering.

The present invention provides methods and apparatuses for creating a high dose of ionizing radiation in unhealthy tissue, such as tumors, while maintaining low dose in nearby, healthy tissue. The method employs a contrast agent to concentrate heavy atoms in the tumor, creating a larger cross-section area in the tumor for absorption of x-ray photons. When a properly configured, preferably optically focused x-ray beam irradiates the contrast agent, significantly more photons are stopped than in the absence of contrast agent. Since most of these increased photon stoppages result from the photoelectric effect, tumor tissue damage will be even higher than without the agent.

The usefulness of the technique lies in the large achievable dose enhancement ratios and the ability to quantitatively verify the amount of contrast agent in the tumor before irradiation. A high dose ratio of x-rays absorbed by the tumor as compared to x-ray absorbed by healthy tissue can be achieved through the methods of the present invention. Achieving a dose about three times higher in a tumor than in healthy tissue is common. Values of ten times higher or more are possible. The prior art has not recognized that ratios higher than about three to one are possible, and that such ratios are very important in treating disease. It is the combination of new contrast agents, new beam designs, new delivery design, and new calibration techniques that make this possible. The key to the invention is to achieve high doses of x-ray in unhealthy tissue only. Thus, success in the invention requires that a variety of techniques be brought together to work in concert.

A. Heavy element contrast agent

The desired effect can only be achieved by having heavy elements present in large amounts at the tumor site. The human body primarily consists of light elements, those in the bottom half of the periodic table. To obtain a major increase in photoelectric absorption from an element at x-ray energies that penetrate significant distances into the body, the absorbing element should have an atomic number of 50 or more. Iodine, at Z=53, is near the bottom of the desired range. Gadolinium (Gd) is better Gold (Au) is nearly ideal, but the x-ray spectrum needs adjustment to stay above the K-edge. Any element with an atomic number greater than that of tin (Sn, element 50) introduced into the targeted tissue with sufficient concentration will suffice. However, as a practical matter, many of the heavy elements are either too expensive or have potential toxicity problems.

Iodine (I, element 53), a common element in contrast media, has its K-edge at 33.2 keV. At this low energy, x-rays penetrate only a short distance into the body, so x-ray sources are mostly configured to operate at energies above 34 keV, and there is no issue of tuning to the element.

However, as the atomic number rises, so does the energy of the K-edge. Gadolinium (Gd, element 64) has its K-edge at 50.2 keV, meaning that any radiation that is emitted by the source below 50.2 keV will be absorbed in the patient without most of the desirable enhancement from the contrast agent. Therefore, when using gadolinium as the contrast agent, the x-ray source output should be filtered to remove most of the flux below 50 keV. On the other hand, because of the higher atomic number, the absorption of each individual atom is higher, providing a better therapeutic ratio per atom in the tumor.

A third element commonly used for contrast is gold (Au, element 79). Its K-edge is located at 80.7 keV. This energy is high, above that of most of the x-rays generated for chest diagnostics and CT. The lower absorption of the 80+ keV photons by the light elements of the body means the beam travels relatively unattenuated deep into the body, then interacts strongly where it encounters a high concentration of gold. Thus, gold, despite its cost, has a very attractive performance.

B. High concentration of heavy element contrast agent

To achieve a major change in the absorption properties of the body, the concentration of the heavy element must be high at the target site and low elsewhere. To make any change in the local x-ray dose, the heavy element must represent at least about 0.1% of the targeted tissue by weight. To get a large (i.e., a factor of two or more) dose enhancement effect, the heavy element should be present in excess of about 1% by weight in the target tissue. The exact enhancement ratio is a function of the contrast agent, source spectrum, and target depth.

Successful contrast agents for diagnostic use require high levels of heavy elements (0.1 to 1% or higher). Iodine contrast agents are most commonly used because they can be introduced into the blood stream in large quantities with minimal toxicity to the patient Thus, iodine is the element of choice for contrast media in x-ray diagnostics, including CT. A typical, modern iodine-based contrast agent can be injected in quantities containing as much as 60 grams of iodine. As this is mixed into approximately 5000 g (5 liters) of blood in the body, the concentration can be over 1% by mass without toxicity to the patient. To achieve this level of concentration requires that the contrast agent be introduced into the blood stream intravenously, in less than a minute. The contrast agent spreads and reaches a tumor anywhere in the body in approximately 3 minutes. The body then expels the contrast agent with a half-life of about one hour. Therefore, the contrast agent is present for only a relatively brief period. The therapy of the present invention should be performed within a half-hour after injection of the iodine if it is to be fully effective. A contrast agent that would remain in high concentration for a period of several hours is preferred.

We have found that intravenous injection can achieve interesting levels of dose enhancement, but usually not a large enough differentiation between tumor and normal tissue to kill the tumor with a single dose without harming surrounding tissue. We have now found and demonstrated that such high levels of dose enhancement are easily achieved if the physician injects contrast agent directly into the tumor or into a portion of its surface and calibrates the amount injected until a desired amount of contrast agent is injected. We demonstrate here that enhancement ratios in excess of two to one are achievable in most tumors, and have injected concentrations sufficient to provide over ten to one enhancement ratios in some cases.

The other very common contrast agent uses gadolinium for MRI diagnostics. It is actually the magnetic properties of Gd that are desired in the MRI. Nonetheless, large quantities of this heavy element are introduced into the blood stream and can be considered for therapeutic work.

C. High differentiation of the contrast agent

A contrast agent is usually injected into the bloodstream intravenously, and it largely remains there. A little diffuses out into the tissue, but for the most part it is removed by the kidneys and leaves the body in the urine, having had very little physical impact on the patient. The half-life for removal of the contrast agent from the blood is typically about one hour. Thus, after intravenous injection of contrast agent, one sees regions containing a high concentration of blood more clearly in an x-ray image.

Tumors, for the most part, differ from healthy tissue in that they have poorly formed blood vessels. The vessels carrying oxygen and nourishment come from outside the tumor and each capillary supplies many tumor cells. As the contrast agent-rich blood passes into the tumor, the walls of the newly, poorly formed, and hypoxic blood vessels allow some of the contrast agent to leak into the tissue. This allows an accumulation of contrast agent substantially greater than in healthy tissue, making the tumor more visible. By forcing significant quantities of the contrast agent directly into the tumor using local injection, very high percentages of contrast agent, and hence dose enhancement, can be obtained. The contrast agent diffuses through the leaky environment of the tumor and then diffuses less rapidly into the surrounding, healthy tissue. Direct injection is also desirable when a tumor sits near a delicate structure like the spinal cord or the optic nerve, even if it takes surgery to deliver the contrast agent, followed immediately by the x-ray surgery. The discrete nature of a tumor structure usually keeps the contrast agent within the tumor and greatly retards leakage into the healthy surrounding tissue. Direct injection of deep tumors requires localization with ultrasonography, CT imaging, or stereotactic guidance. The ability to target only the surface portion of the tumor mass makes feasible the delivery of contrast agent by injection to tumor masses greater than 1 cm in diameter.

Contrast agents that specifically bind to tumors, for example, by using antibodies, peptides, or nucleic acids, also can make the contrast agent specifically target tumors. Such improvements can, in principle, further extend the contrast and hence the differentiation of the dose in the target from the dose in the healthy tissue.

D. Optimized x-ray spectrum

Since x-ray dose enhancement relies on a significant number of x-rays being stopped by photoelectric absorption as opposed to Compton scattering or elastic scattering, optimizing the spectrum of the ionizing radiation also is important. As the energy of the x-ray photons increases above the K-edge, the probability of an interaction through the photoelectric effect drops dramatically relative to the probability of a Compton effect interaction. As photon energy nears 1 MeV, the contribution from the photoelectric effect becomes insignificant, making the energy dose deposition at the tumor purely a function of tissue density, with no discernible effect from tissue composition. In fact, above 150 keV, the energy range of CT scanners, the number of photoelectric interactions approaches zero. Thus, as the energy of the incident photons climbs, the dose enhancement falls. Similarly, as the energy of the photons falls below the K-edge of the absorber in the contrast agent, the dose enhancement falls. Thus, the x-ray spectrum must be optimized for maximum effect. The present invention uses an x-ray apparatus with an output of about 30 keV to about 150 keV, which is defined herein to be "orthovoltage." Preferably the output is about 40 keV to about 80 keV. Such radiation requires only a conventional x-ray source instead of a linear accelerator or radioactive source, as used to create MeV beams, or the sources for CT scanners. This is a major advantage over conventional systems used for x-ray therapy and x-ray surgery based on cost considerations.

Electron impact x-ray sources emit primarily bremmsstrahlung radiation, which is intrinsically continuum emission. Even with glass and aluminum filters in the path of the x-ray beam, the typical spectrum covers over a factor of two in energy from the low-energy to the high-energy cutoffs. Since photoelectric absorption scales roughly as the cube of the photon energy, there is nearly an order of magnitude change in the size of the dose enhancement effect across the spectrum. Thus, the photons at the low-energy end of the bandpass, that is, in the orthovoltage range as defined above give the dose enhancement, but tend to be absorbed before reaching the target. The photons at the high-energy end deposit relatively little in the target because of lower absorption in the contrast agent. Thus, a properly configured filter would have no more than about plus or minus 25% spread in energy width, e.g., centered at about 60 keV and stretching from about 40 keV to about 80 keV. This leads to a optimal performance.

With a standard exit filter on the x-ray-generating machine, the spectrum can be cut off at the low-energy end with a simple increase in absorber thickness. Unfortunately, this is a gradual cutoff in throughput. At the high-energy end, the sharpness of the cutoff can be increased using a filter of a rare earth like dysprosium. At the bottom end, conventional absorption filters help, but a multilayer mirror as described hereinbelow is best.

Overall, the effectiveness of this technique is less sensitive to exact spectrum than one might suspect. As the energy above the K-edge increases, the probability for absorption decreases; however, the energy of the photoelectron increases, creating more local biological damage. Thus the technique can be applied effectively without fancy filtering—it is merely a little less optimized.

E. High-intensity beam

Another major factor that has stopped the practical application of the use of contrast agents for x-ray therapy and x-ray surgery is, as discussed above, the relative rapidity with which the contrast agent is flushed from the body. The amount of an agent in the body can be significantly reduced in as little as ten minutes. As such, there is limited time during which the procedure can be done effectively. To counter the limited time, one should use a high-intensity beam that can reach high dose levels quickly.

A variety of techniques can be brought to bear on this problem. First is the application of bright beams. The brightest sources in general use are those in CT machines, where the need for excellent signal has driven the development of source brightness well beyond that needed for normal diagnostics. Bright x-ray sources can now operate at continuous power in excess of 5000 W (e.g., 50 milliamps at 100,000 V). However, sources tend to be limited by the amount of power that can be dissipated by the electron target. Thus, to achieve even higher source flux requires both higher performance power supplies and better cooling systems.

The patient should be moved close to the source. The casing around a typical source extends about 40 cm beyond the target. Thus a patient cannot be much closer than about 50 cm from the x-ray source. Specially packaged sources that allow the patient to be placed 30 cm from the source instead of the usual one meter will lead to a flux increase of an order of magnitude, and such sources are used in the present invention. The treatment should be completed as quickly as possible. We have been able to treat in 10 minutes with a relatively weak source. The newer, more powerful sources will deliver enough flux to complete the therapy an order of magnitude quicker.

F. Geometry of the beam

The contrast agent alone can give excellent ratios of skin dose to tumor dose in many cases. In cases where the contrast agent does not settle into the tumor in high concentration, and where the tumor is deep within the body, further suppression of the dose to healthy tissue is desirable. This can be accomplished by moving the x-ray source. A series of exposures in which the beam is aimed at the tumor from different directions will keep a high dose on the tumor while spreading dose to healthy tissue over a much larger volume, significantly reducing dose to the healthy tissue. Similarly, one can move the x-ray source through a series of arcs in the manner of radiosurgery. Yet another improvement in the distribution of the x-rays to the interior to the body can be achieved by modifying the size and shape of the beam as it moves. Improvements in beam geometry are completely complementary to the pharmaceutical dose enhancement, and both techniques benefit from the simultaneous application of the other.

G. X-ray concentration

Figure 3:
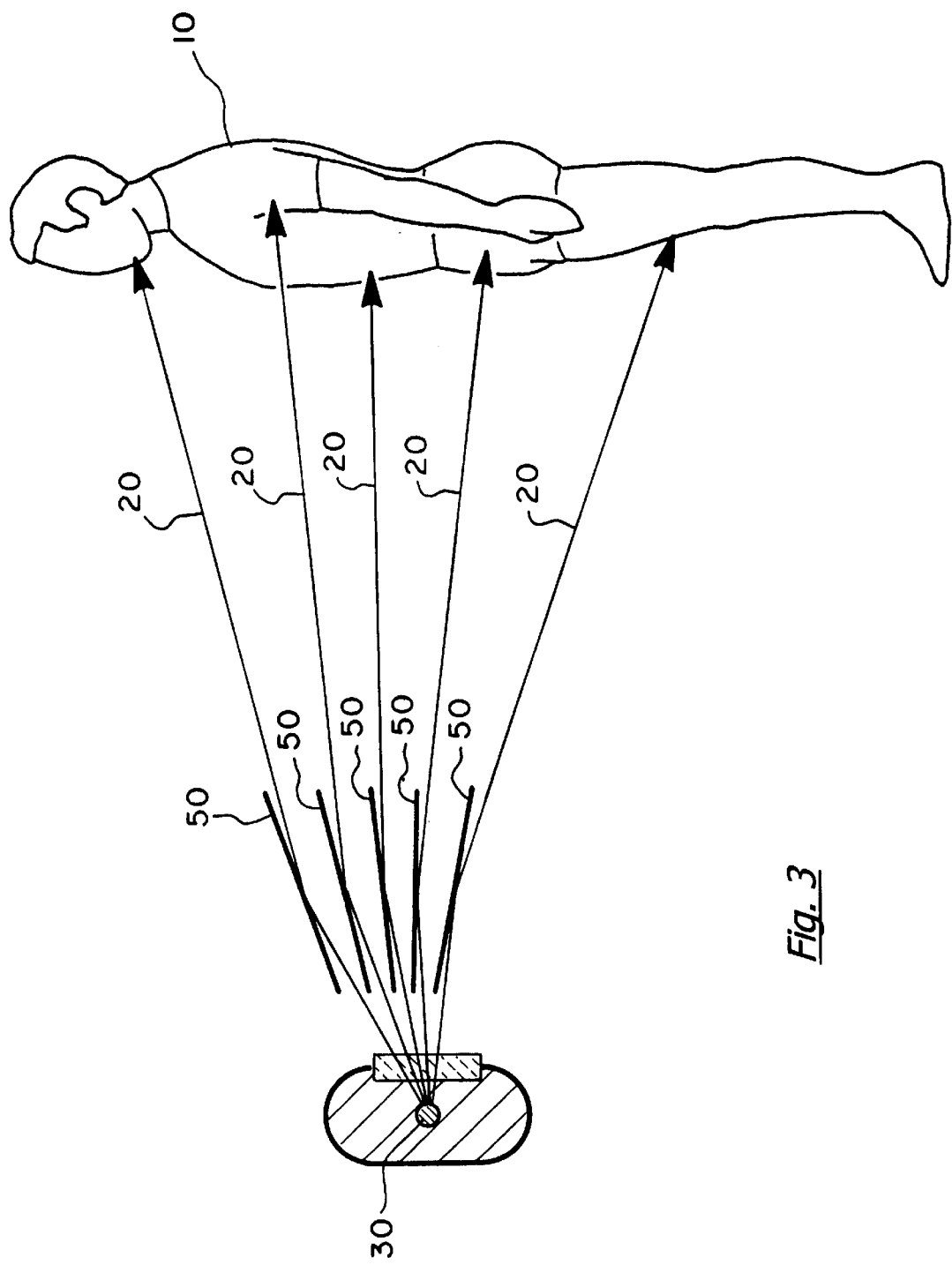
FIG. 3 illustrates radiotherapy using orthovoltage performed with a mirror array.
Figure 4:
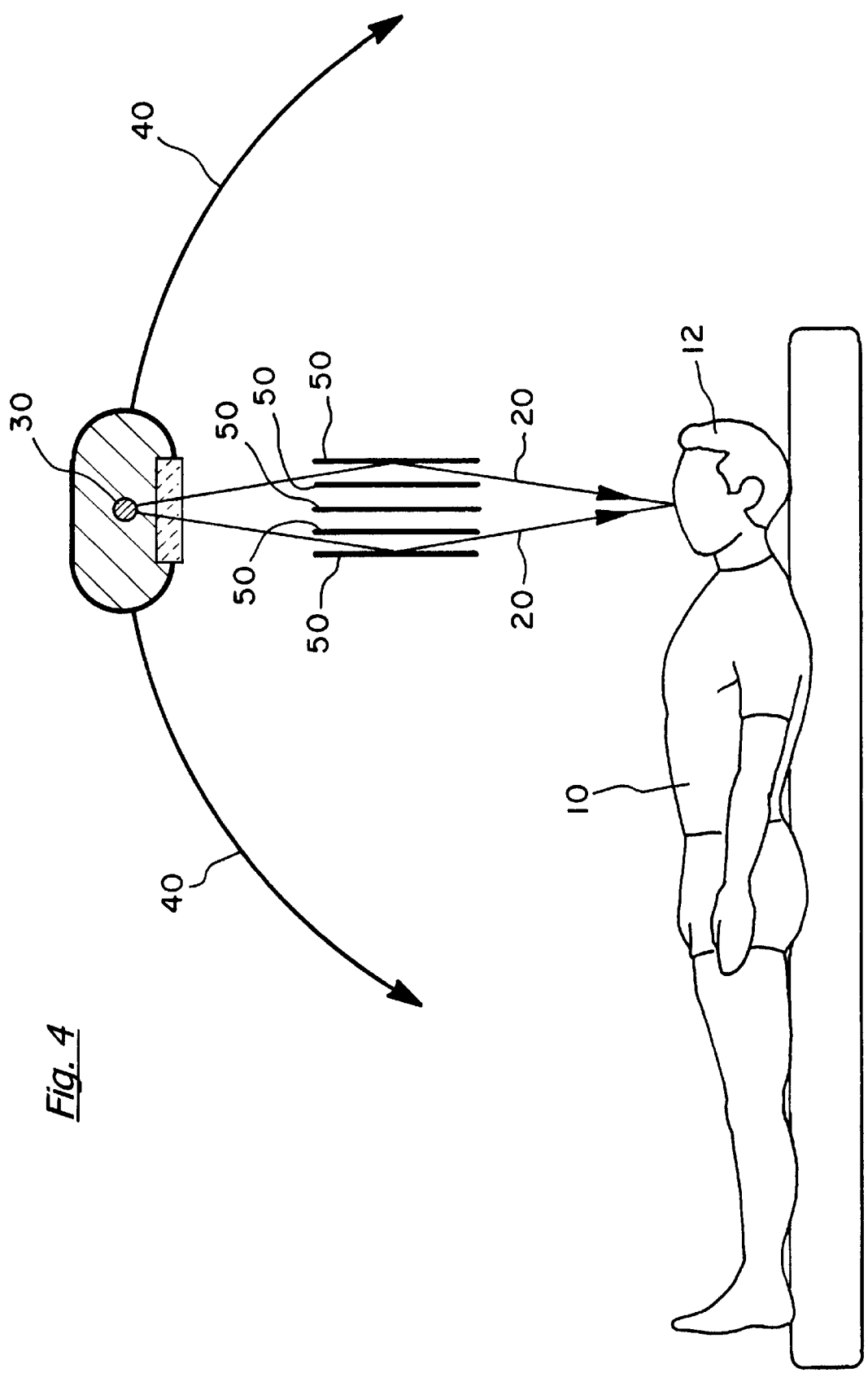
FIG. 4 shows radiosurgery with a mirror array.

Using CT scanners and arcs of the kind that are used in radiosurgery can increase the level of dose in the target relative to that in the healthy tissue. However, these methods will not speed up the deposition of dose. Focusing x-rays with a mirror array does increase dose deposition speed. The mirror array allows a more efficient system. Such a system is illustrated in FIGS. 3 and 4. As shown in FIG. 3 for radiotherapy and in FIG. 4 for radiosurgery, the mirror array 50 creates a more intense x-ray beam 20 and filters the spectrum to close to optimum. The mirror array 50 catches x-rays 20 that would otherwise miss the tumor, or, more likely, strike a collimator surface and be absorbed before reaching the patient 10. This is the ideal approach to solving the speed problem, as it does not require huge increases in source capability to achieve major speed increases. In addition, the beam becomes more intense as it approaches the target as opposed to the divergence losses in an unfocused system.

Figure 5:
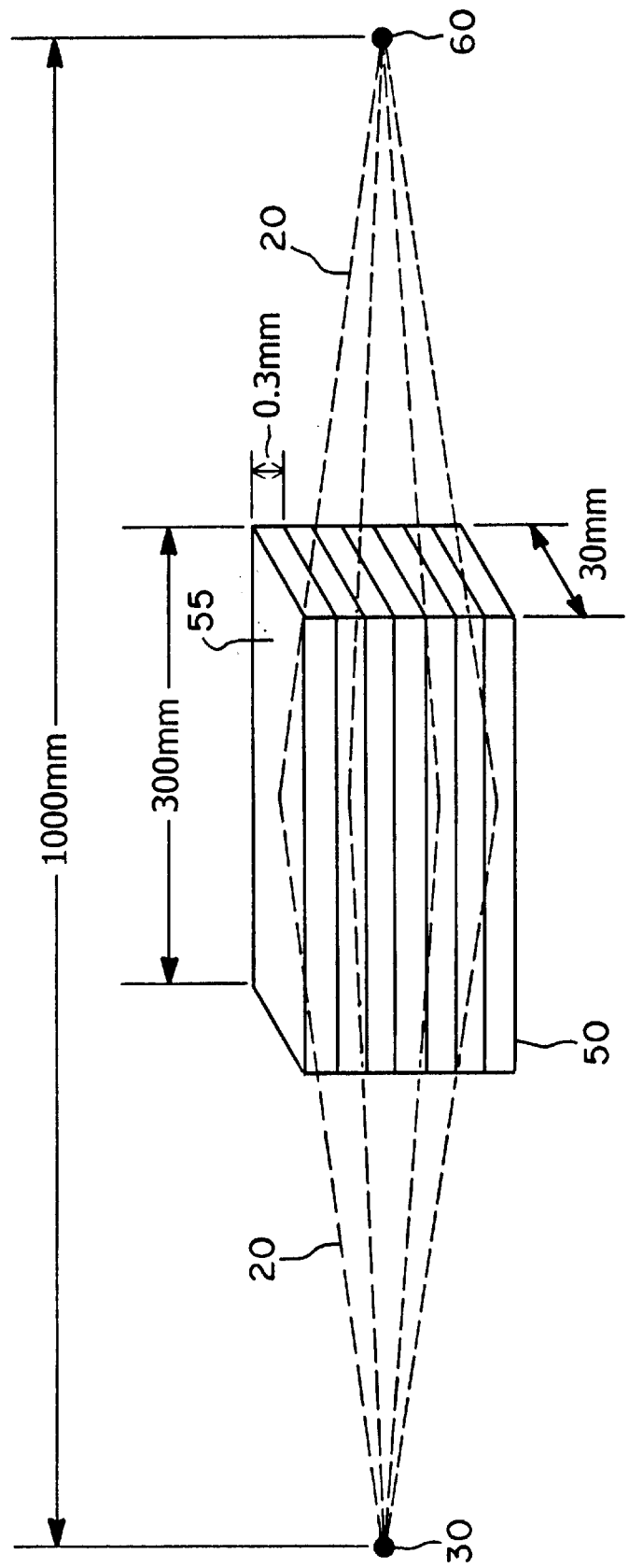
FIG. 5 illustrates a mirror array that concentrates x-rays.

In a preferred embodiment as shown in FIG. 5, an array 50 of mirrors 55 approximately 300 mm long and 30 mm wide arranged to converge, or focus, x-rays 20 is useful in the invention. The mirror array 50 can be considered a lens, and is sometimes referred to as a lens in this specification. The x-rays 20 diverge from the x-ray source 30 until they reach the mirror array 50, which focuses them to a desired target 60, such as a tumor. The mirror array 50 functions at any x-ray energy up to about 100 keV, but will not function in the regime above 1 MeV. The application of these kinds of mirror arrays 50 in medical x-ray devices is unique. In fact, prior medical x-rays have diverged or weakened as they travel from the source 30 to the target 60.

Figure 6:
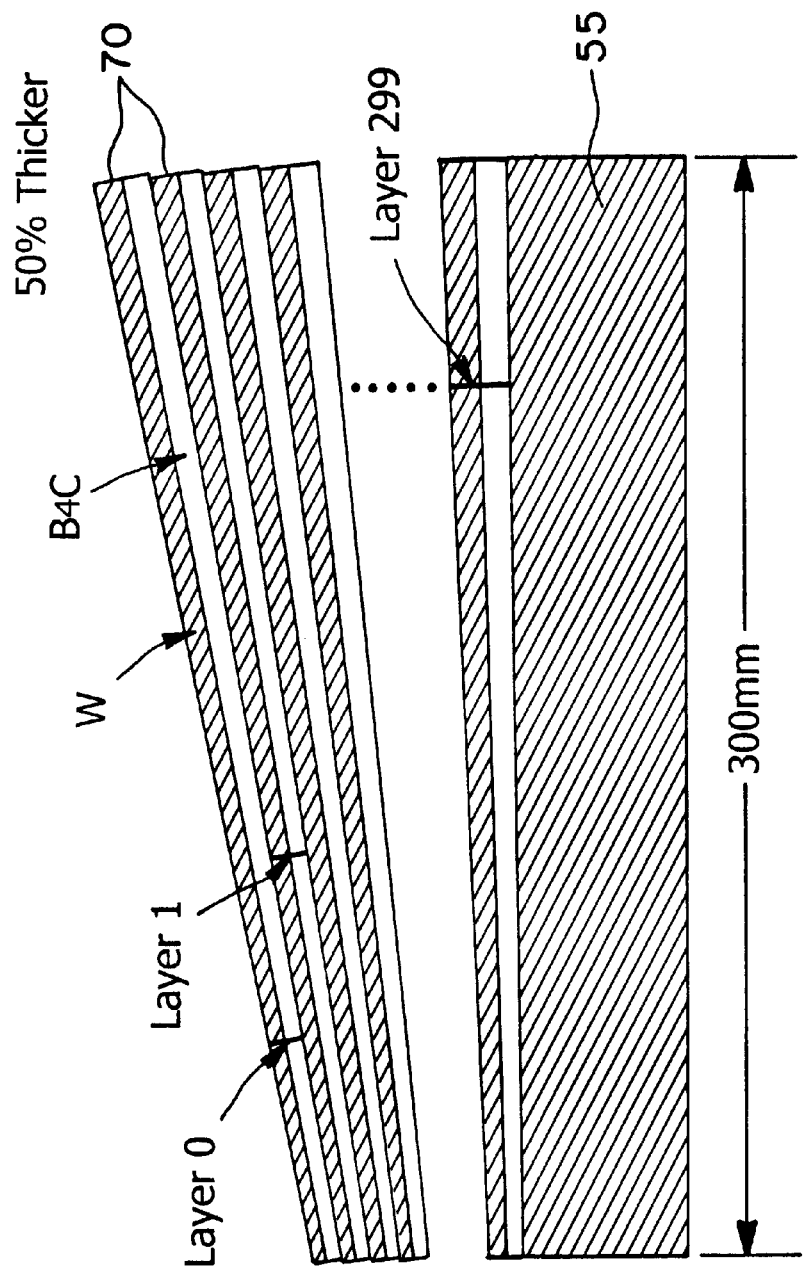
FIG. 6 illustrates a graded multilayer applied to each mirror in the array of FIG. 5.

Efficient concentration of x-rays 20 requires that the reflection occur at a very low grazing angle of below a half-degree. As shown in FIG. 5, a mirror array 50 that concentrates x-rays 20 can be built from an array of thin substrate flats or near-flats acting as mirrors 55. The x-rays 20 reflect at grazing incidence. As FIG. 5 illustrates, each mirror 55 is about 30 mm wide, about 300 mm long, and about 0.3 mm thick and is polished to support graded multilayers to support high reflectivity at higher grazing angles. Each mirror in the array can be coated with up to 299 graded multilayers 70 as illustrated in FIG. 6 to increase the graze angle, increase the reflection efficiency, and filter the beam spectrum. To achieve the desired optical throughput, layering 70 on the mirrors 55 must compensate for position along both the length and the depth of the mirror 55, as shown in FIG. 6.

Figure 7:
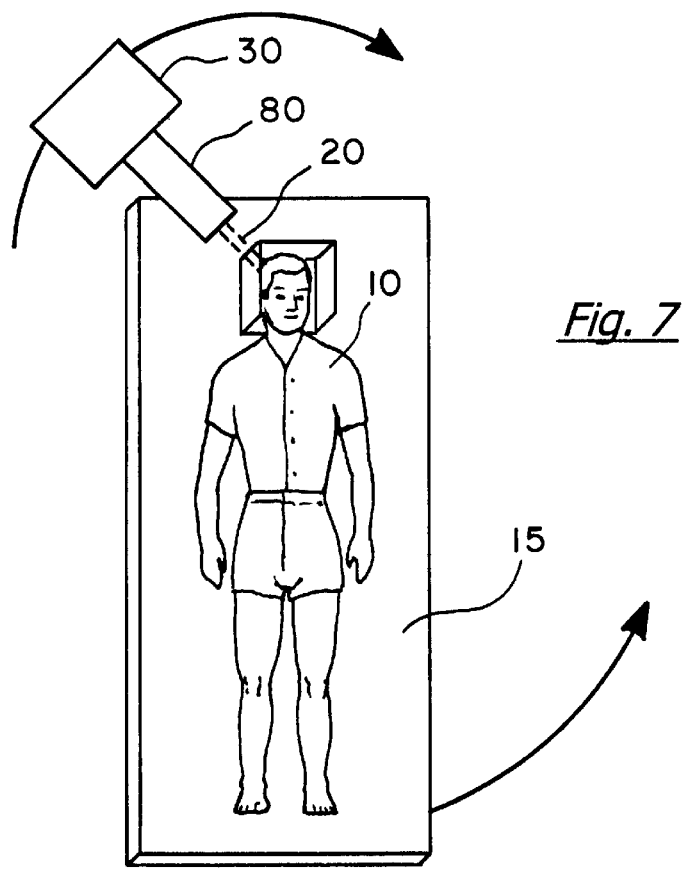
FIG. 7 illustrates the mirror concentrator array of FIG. 6 mounted to the casing of a standard orthovoltage x-ray source.

The x-rays 20 emerging from the mirror array 50 diverge in the dimension parallel to the mirror 55 surfaces, as shown in FIG. 5. At a distance of one meter from the source 30, the reflected beam of x-rays 20 converges to a line 60 approximately 1 mm wide and approximately 50 mm long. A pair of shutters, or jaws, that can be electronically manipulated during radiosurgery to match the tumor shape can shorten the length of the line. The mirror array 50 is mounted in a box 80, as illustrated in FIG. 7, and affixed to the output side of a standard orthovoltage x-ray source 30. Both the x-ray source 30 and the table 15 on which the patient 10 is placed are rotatable, as shown by the arrows in FIG. 7. Thus, concentrated radiation can be combined with desirable arc geometries.

Because the focused beam 20 increases the amount of power delivered to the target, treatment time is greatly reduced. The lens formed by the mirror array 50 also shapes the beam 20 into tight geometries, thus keeping unwanted radiation from damaging healthy tissue just outside the tumor. Moreover, unwanted radiation is also reduced in the path of the x-ray beam 20 in front of and behind the tumor.

The reflection properties of these special mirrors 55 create a quasi-monochromatic response in the output of the system. The subsequent spectral shape is instrumental in reducing unnecessary doses of low-energy photons that are otherwise absorbed in healthy tissue. If the narrow, reflected band includes a strong emission line from the source 30, the total flux can remain quite high. These factors lead to an efficient lens, optimized for medical applications.

Treatment with these mirrors 55 can be performed with a one-dimensional concentration. However, two-dimensional focusing may be preferable in order to provide faster, more precise patient treatment.

A two-dimensional lens (not illustrated) concentrates the x-ray beam 20 in two dimensions. It consists of two one-dimensional lenses mounted in sequence, orthogonally about the central axis. A two-dimensional lens focuses to a smaller spot and is thus ideal for high precision work. The treatment of any but the smallest tumors (i.e., greater than about 7 mm diameter) is more difficult because the dose deposition requires a two-dimensional "painting" with the x-ray beam 20. Use of the beam 20 in such a manner may be advisable in delicate cases, but for large tumors, treatment with a one-dimensional lens may be preferable. Treatment choice between one-dimensional and two-dimensional lenses will be determined in time by experienced doctors. For specific lenses that can be used as described herein, see U.S. Pat. No. 5,604,782, U.S. provisional patent application 60/039,346, filed Mar. 18, 1997, and PCT/US98/05219, filed Mar. 17 1998, all of which are incorporated herein by reference.

Figure 15:
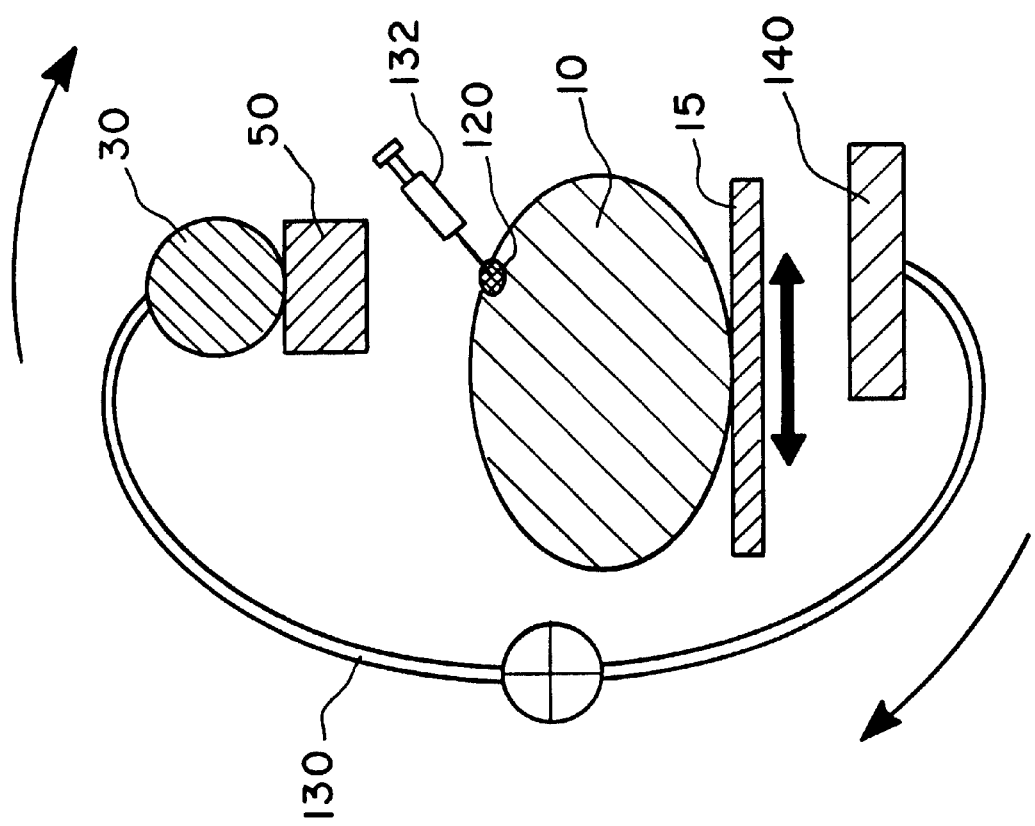
FIG. 15 demonstrates the direct injection of a tumor with contrast agent.

All the needed capabilities to support the practical application of dose enhancement therapy can be combined in a machine 130 like that illustrated in FIG. 15 and FIG. 16. The patient 10 is placed on a movable table 15. The lens 50 is not necessary for all applications, and can be replaced with a simple aperture stop. The patient 10 is injected 132 with contrast agent preferably directly into the tumor 120, and is situated with the tumor 120 at the center of the arc of rotation, which is indicated by the arrows in FIGS. 15 and 16. Before the contrast agent flushes from the tumor 120, the machine 130 is moved through its arcs, as shown in FIGS. 16A and 16B. A modern angiography x-ray source is bright enough to expose the patient 10 in the half-hour that is typically available, even without the concentrating power of a lens 50.

A useful feature of the machine 130 is a monitor 140 which consists of a lower power digital x-ray diagnostic system, that would support real-time tracking of the contrast agent density in both the normal and diseased tissue. This would allow for real-time adjustment of dose, and precision of dose levels unavailable without direct knowledge of the pharmaceutical levels.

H. Calibration

In nearly all uses of contrast agents, after introduction of the agent into the body, the distribution of the drug is assumed, not actually tracked and measured. We have found that it is crucial to the present invention to quantitatively measure the amount and distribution of the contrast agent before irradiation. The contrast agent must reach a substantial portion of the target and must reach a minimum level if the desired differentiation of response is to be achieved.

We have found through application of physics, x-ray cross sections, and computer modeling that the dose enhancement generated in a target is given in a first preferred embodiment by the equation de=1+1.3 p (de is the dose enhancement ratio, which is the number of cGy experienced by the tumor injected with contrast agent divided by the number of cGy in the adjacent tissue without contrast agent; p is the percent contrast agent by weight in the tumor). This is for the case where the contrast agent is iodine base, the beam is from a tungsten target electron impact source run at 125 kVp with 3 mm Al equivalent of filtering, and the tumor is near the surface of the body. Thus, at least 0.75% iodine by mass must be injected if a dose enhancement ratio of 2:1 is to be achieved. The exact formula is adjusted slightly if the beam, the contrast agent, or the depth is significantly different. For example, if the target tumor is deep, then relatively little of the low-energy end of the spectrum will reach the target, lowering slightly the de. If the beam itself is weighted to the low end, then this effect will be enhanced. If the contrast agent used is something other than iodine (e.g., gadolinium), then the de is also affected. Each of these effects can be accounted for quantitatively.

Once de is determined, a preferred approach is to irradiate the patient 10 so that the tumor receives 1600 cGy in a single dose, and the surrounding healthy tissue receives 1600/de cGy. With values of de in excess of two this is a safe and robust way to kill targeted tissue.

In a second preferred embodiment, the method for determining the value of de is to put the patient 10 in a CT scanner 130 and perform the injections there, as shown in FIG. 15. The needle 132 can be directed by iterative use of the CT scanner 130. When the tip of the needle 132 is in the tumor 120, the doctor injects the contrast agent and takes another CT scan. The value of de is then directly calculated by de=1+0.0025 H where H is the Hounsfield number of the tumor 120 read directly from the CT screen. Iteration between injection and CT scans continues until the contrast agent is distributed to the desired level or higher across the bulk of the target.

The Hounsfield number H is defined as:

$$H = 1000 \frac{\mu - \mu_0}{\mu_0},$$

where $\mu$ is the local absorption coefficient and $\mu_0$ is the absorption coefficient of water. Absorption coefficient is defined as $\delta I=-I\mu\delta x$ where $\delta I$ is the change in the intensity of a beam of intensity I as it passes a distance $\delta x$ through the body.

In the event that the tumor 120 is near the surface, the needle 132 can be guided by eye for the injection. Calibration of the amount of contrast agent also can be accomplished with any standard x-ray diagnostic machine equipped with a digital readout. Digitization of film is impractical due to the length of time required for an iteration; however, fluoroscopes equipped with digital readout will show a significant loss from the contrast agent For example, an injected site that would present in a CT scan with a Hounsfield number of 400 (de of 2) would absorb 33% of the beam, creating an easily calibrated shadow. Assurance of uniformity of dose enhancement is poorer than with a CT scan because of the lack of depth information. However, two images from different angles can at least give some idea to the doctor of the overall distribution of contrast agent within the target tumor.

To inject a target that is not near the surface of the body without a CT, ultrasonography is preferably used to guide the needle, combined with a fluoroscope 140 to calibrate the amount of contrast agent.

I. Prescription of Dose

Conventional radiotherapy and past attempts at increasing the effects of treatment have used small daily doses of radiation delivered over many weeks. Small daily fractions decrease the chance of injury to the normal tissue but also decrease the chance of controlling the tumor. Because the deposition of radiation by the method of the present invention conforms so precisely to the volume of the tumor, it is possible to deliver very high doses of radiation in one or two fractions without the risk of substantial injury to the normal, surrounding tissues. The liquid contrast agent conforms to the dimensions of the tumor and spares the healthy cells when injected. The incident treatment beam does not require mechanical collimation in this case. A dose of radiation that is well within the tolerance of the normal tissues is prescribed to the area around the tumor, and the augmentation of radiation dose is confined to the malignant mass. We refer to this method as liquid, conformal radiosurgery (precision, high dosage, and low numbers of fractions of radiation), to distinguish it from conventional methods that employ alloy masking or multi-leaf collimation of the radiation portal to spare the normal areas. Such expensive devices are not required by the present invention, yet the conformal delivery of the radiation dose appears to be more precise.

J. Helper Effect of the Agent

We have treated three patients and eight lesions with contrast-enhanced, orthovoltage radiosurgery according to the methods of the present invention, as described in more detail below. After calibration of the maximum and minimum augmented doses to the tumor, we believe that there is an effect in killing the tumor that goes beyond what would be expected from the delivered doses. We believe that the interaction of the orthovoltage x-ray with the contrast agent produces iodine radicals that are extremely noxious to tumor cells. The effect is very specific to the lesion, as we noted that the normal skin over an ulcerated tumor healed without delay following treatment. Rapid healing of an ulcer would not expected if the normal tissues had received the high doses. This suggests that the fall-off of the high doses around the concentration of contrast agent within the tumor occurs within millimeters. In addition, we believe this technique is extremely efficient at destroying the tumor's blood supply. The contrast agent pools in the vasculature of the tumor (even when directly injected) and the highest concentrations of the heavy metal are achieved in the periphery of the lesion where the blood vessels enter the tumor.

K. Treatment of the Surface Portion of the Tumor

Conventional radiation dosing of tumors requires maximum input to the center of the lesion. The center of most tumors tends to be hypoxic and necrotic, conditions that have been shown to produce resistance to radiotherapy. The methodology of the present invention of injecting tumors in a surface portion with contrast agent overcomes the problems of inadequate uptake by the intravenous route and inconsistent concentration by direct injection. The large increase in dose delivered to the surface of the mass selectively destroys its blood supply, and since each capillary supplies many tumor cells, the destruction of the tumor is enhanced. The central, necrotic, and radioresistant portion of the tumor is thus destroyed with a lower integral dose of radiation to the normal tissues struck by the beam in transit.

The method for delivering a desired amount of contrast agent to a surface portion of a tumor mass is illustrated in FIG. 17, which shows a tumor 120 lying within normal tissue 115 of a patient 10. The injection of a surface portion 124 of the tumor 120 is preferably performed in tumors 120 with a radius of at least about 2 cm (20 mm). The delivery of the contrast agent to the surface portion 124 is visualized either directly or by ultrasonography, CT scanning, or fluoroscopy as described above. A desired amount of contrast agent is injected by hypodermic needle 132 into the surface portion 124 of the tumor 120, avoiding the interior 122 of the tumor. At most, the surface portion 124 excludes the interior 122 of the tumor 120 up to about 50% of the radius of the tumor 120. That is, if a tumor 120 has a radius of 5 cm (50 mm), the surface portion 124 may extend as far as about 2.5 cm (25 mm) toward the center of the tumor 120. The surface portion 124 preferably extends into the tumor 120 up to about 20% to about 30% of the radius. For example, in a tumor 120 with a radius of 5 cm (50 mm), the surface portion 124 that is injected with contrast agent is about 1 cm (10 mm) to about 1.5 cm (15 mm) deep and extends around the entire surface of the tumor 120.

Thus, the present invention comprises a method for treating tumors 120 by pharmaceutically enhanced low-energy radiosurgery with focused x-rays beams 20 that includes the steps of delivering a desired amount of a contrast agent, preferably by injection either intravenously into the patient 10 or directly into the tumor 120, or into a surface portion 124 of the tumor 120. The delivery of contrast agent can be monitored by ultrasonography, CT, or fluoroscopy. The amount of contrast agent within the tumor 120 is then calibrated in order to determine a desired x-ray dose enhancement in the tumor 120 compared with the surrounding normal tissue, which contains less or no contrast agent. The calibration of the amount of contrast agent within the tumor is preferably performed by using at least two equations. The first equation measures x-ray dose enhancement de on the basis of the weight percent p of contrast agent within the tumor 120, that is, by de=1+1.3 p. The second equation measures x-ray dose enhancement de on the basis of the Hounsfield number H for the contrast agent in the tumor 120 that is, by de=1+0.0025 H. The Hounsfield number H is determined by placing the contrast-agent injected tumor 120 in a CT scanner and measuring the Hounsfield number H directly off the display screen of the CT scanner. The delivery of the contrast agent and the calibration of the amount of contrast agent to determine the desired amount of x-ray dose enhancement in the tumor 120 are repeated until the desired amount of dose enhancement is achieved, preferably from about 2:1 to about 10:1 compared with the dose in normal tissue. The tumor 120 is then irradiated with a focused x-ray beam 20 having an energy level of about 40 keV to about 80 keV. The x-ray beam 20 is focused by the mirror array 50 described hereinabove and in U.S. Pat. No. 5,604,782 and U.S. provisional patent application 60/039,346, filed Mar. 18, 1997, now PCT/US98/05219. The present invention can be further understood in view of the following examples.

EXAMPLE 1

We use for this example a modern angiography x-ray source 30, which operates at 50 mA and 100 kVp continuously for about 20 minutes. A standard efficiency factor for such a source 30 predicts a flux of 6.5 W/steradian. At a distance of 500 mm, this represents $2.6 \times 10^{-5}$ W/mm² impacting the patient. Since the beam loses approximately 2% of its flux per millimeter of tissue traveled, the flux of x-rays scattered from the beam is $5.2 \times 10^{-7}$ W/mm³. However, because the cross section is dominated by Compton scattering which, on the average, retains only 20% of the incident flux for ionization, while sending 80% away in scattered radiation, the total density of ionizing energy is about $10^{-7}$ W/mm³, or 10 cGy/s at the skin. This falls to 3.5 cGy at a typical tumor depth of 50 mm.

Iohexol (sold as Omnipaque™ by Nycomed of Princeton N.J.) is a tri-iodinated molecule that remains undissociated in water, and is 35% iodine by weight. When used as a contrast agent for CT imaging, the standard intravenous dose to a patient is 240 ml, containing 60 g of iodine. Assuming the patient has 5 liters of blood, the iodine will become 1.2% of the bloodstream by weight.

The patient is dosed with 52 keV x-rays. At this energy, the cross section for oxygen atoms is 0.211 (cm²/g) compared to 11.27 (cm²/g) for iodine. Thus, with 1.2% of its mass in iodine, the blood will have 64% greater stopping power for diagnostics. If we assume that the contrast agent accumulates in the tumor at about the same concentration to be found in the blood, then the local cross section in the tumor will rise to 1.64 times that found in the healthy tissue.

Since each iodine interaction is through the photoelectric effect, each interaction deposits half the photon energy as local ionization. The other half of the photon energy escapes as fluorescent (28 and 32 keV) photons. Those photons that interact with the oxygen deposit, on average, 20% of the photon energy, because we get 10% local deposition from the 90% of the interactions that are Compton, and 100% local deposition from the 10% that are photoelectric. The overall dose is thus increased by 160%, for a factor of 2.6 overall. This ratio is high enough to kill the tumors without hurting healthy tissue. The potential integral dose to the normal tissues does not reach clinical significance with this high a ratio. Thus the irradiation creates 3.5 cGy/s in the healthy tissue just outside the tumor, and 9.3 cGy/s inside the target. In under three minutes the tumor achieves 15 Gy, a dose that will fully necrose the tumor. Simultaneously, the tissue around the tumor absorbs only 5.7 Gy, a dose that allows full recovery. At the skin, a dose of 10 Gy accumulates, which is too high for healthy skin. Thus, the treatment is split into at least five shots from different directions of 20 seconds each. Then, none of the patient's healthy tissue experiences a severe dose, and the tumor, as defined by the leaky blood vessels, dies.

It should be noted that concentrations of contrast agent this high are not always possible to achieve by intravenous injection. Thus, direct injection of the tumor is the preferred method.

EXAMPLE 2

Figure 8:
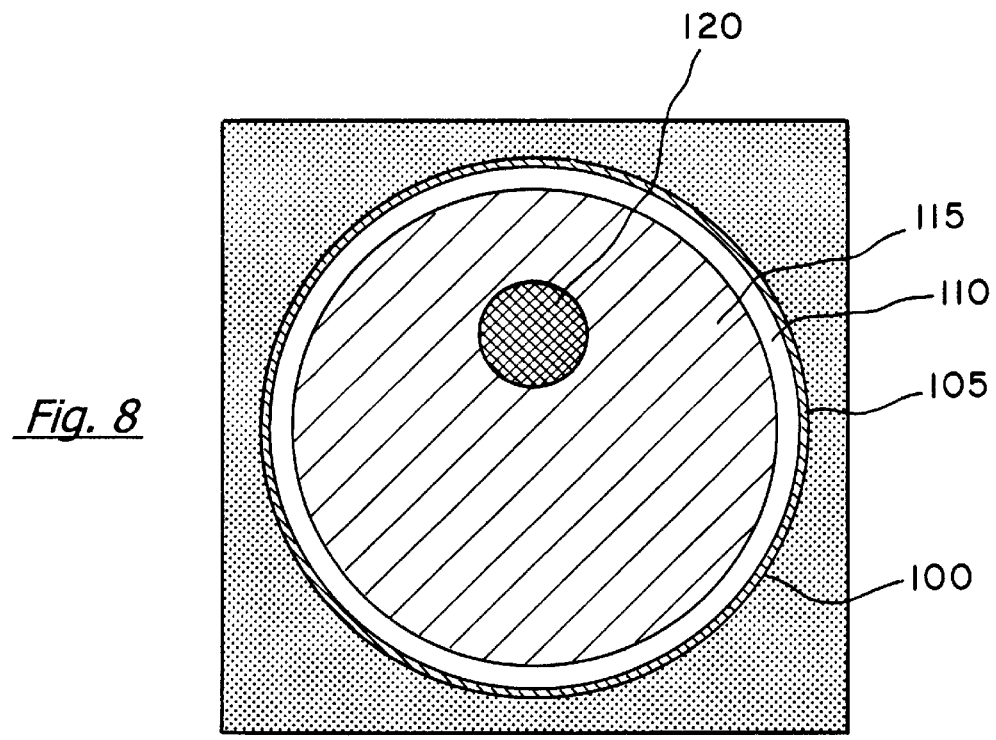
FIG. 8 shows a model featuring a spherical head of 156 mm diameter. It includes a layer of skin, then bone, and is filled with brain tissue. 50 mm deep (28 mm off-center) is a 30 mm diameter tumor, which is to be treated.

The second example was modeled in a computer, as illustrated in FIGS. 8 through 14. We created an approximation to a human head, as shown in FIG. 8, a sphere 100 of radius 78 mm, containing 2 mm³ pixels. Each pixel was assigned a composition and density. The outer layer 105 represented skin, followed by an inner layer 110 representing the bone of the skull. The bulk of the volume 115 represents regular body tissue, which represents the brain and its fluids. A 30-mm-diameter tumor 120 was located 50 mm deep (28 mm off center), and was given the same composition as tissue, but could include an additional 2.4% iodine by weight.

Figure 9:
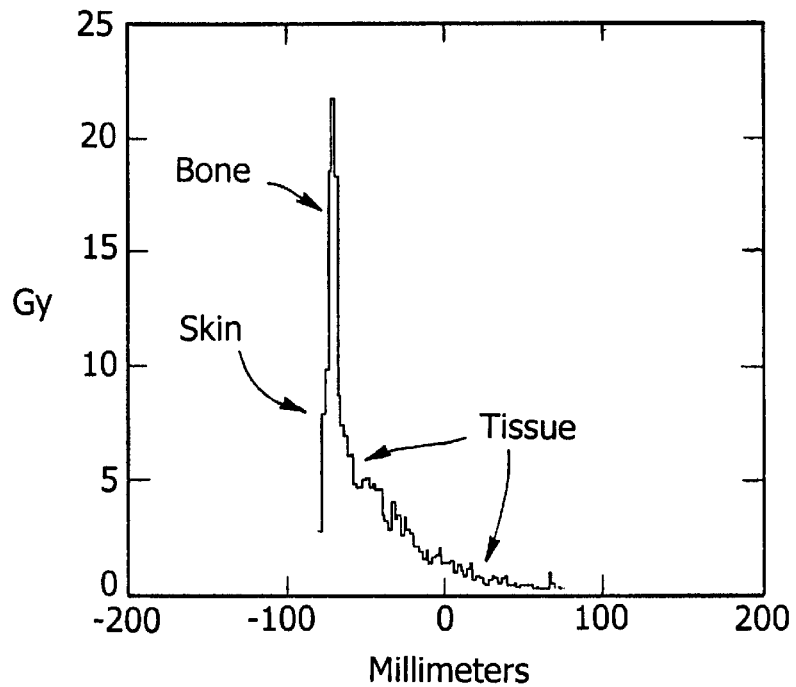
FIG. 9 illustrates the dose distribution as a function of depth when the model of FIG. 8 is irradiated with a 57 keV beam that is diverging from a source 1 meter away.
Figure 10:
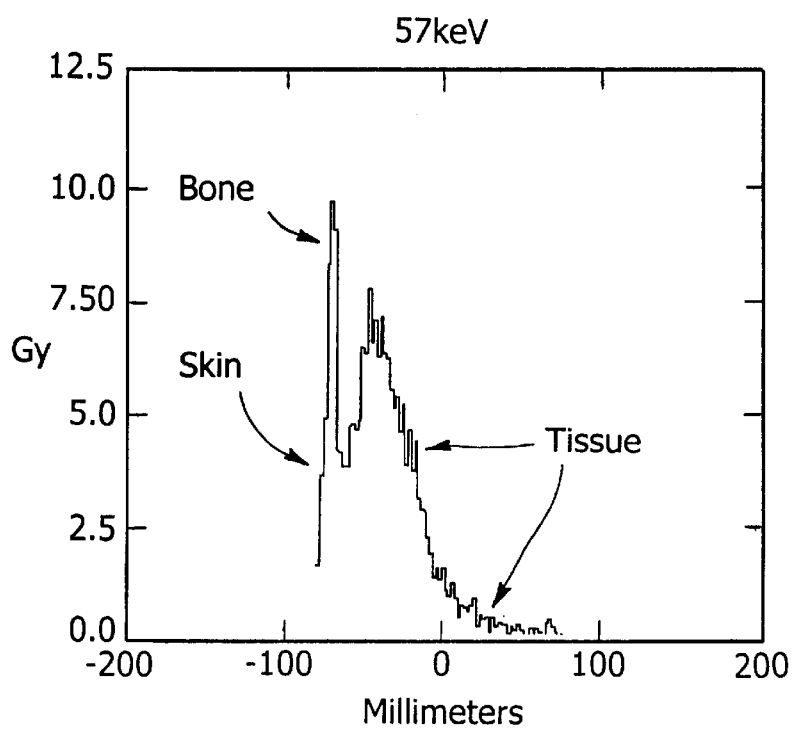
FIG. 10 illustrates a graph of the x-ray dose distribution for the beam of FIG. 9 run through 3 arcs of 120 degrees each.
Figure 11:
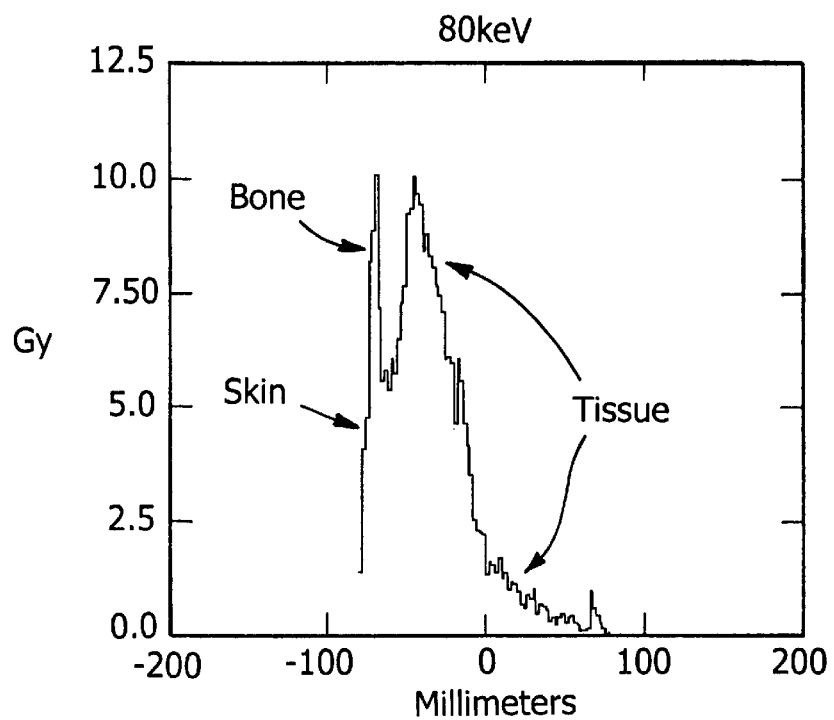
FIG. 11 is the same as FIG. 10, but with a beam of 80 keV.

Individual rays (not illustrated) were traced through this model 100 in a Monte Carlo fashion, to quantify the effects of beam shape and energy, and composition of the tumor 120. The first beam featured a 57 keV x-ray beam diverging from a 1 mm spot, 1 meter away. FIG. 9 illustrates the dose distribution resulting from such a beam, which remained fixed for the entire exposure. The dose is large at the skin layer 105, jumps higher as it passes through the bone layer 110, and is three times lower than the skin dose by the time it reaches the tumor 120, as shown in FIG. 9. The situation can be significantly improved by utilizing the technique of radiosurgery, where the source is swung through multiple arcs with the tumor at the isocenter. In FIG. 10 we show the dose as a function of depth when three 120-degree arcs are used to spread the skin 105 dose and concentrate the tumor 120 dose. However, the dose to the tumor 120 is not much higher than the dose to the skin layer 105, and much of the highest dose is found in the layer of brain tissue 115 outside the tumor 120, where it does damage, not good. A shift to 80 keV resulted in approximately the same profile, but the relative dose in the bone layer 110 was lower, as illustrated in FIG. 11.

Figure 12:
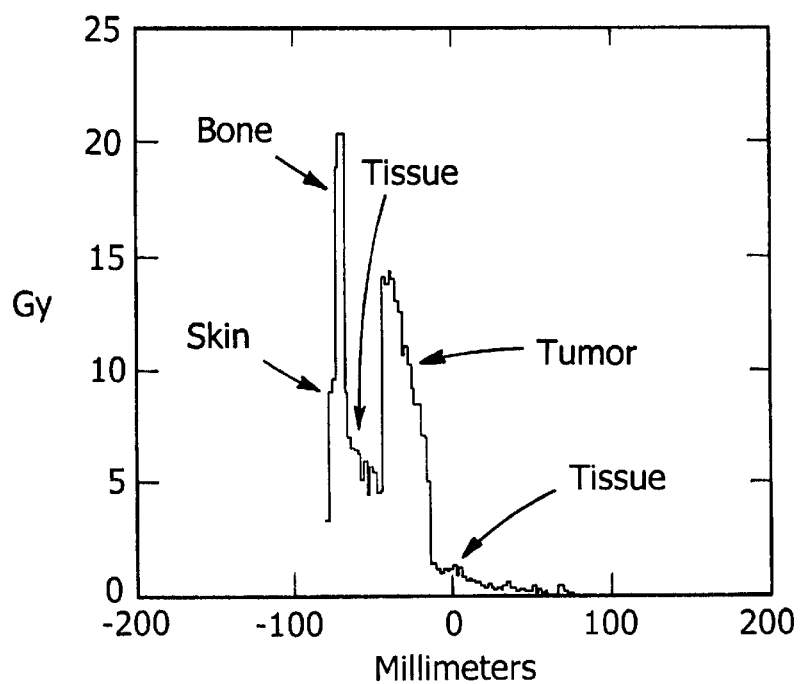
FIG. 12 shows the results obtained when the model of FIG. 8 is treated with iodine and irradiated with a straight beam without arcs.
Figure 13:
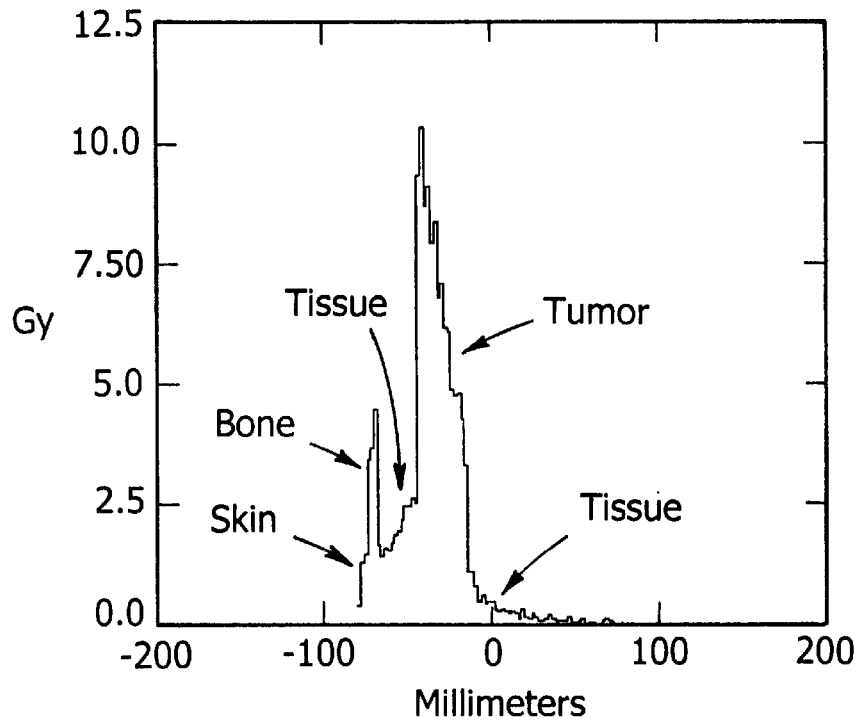
FIG. 13 illustrates the results obtained when the model of FIG. 8 is treated with iodine and the beam is moved through the three arcs of FIG. 10.
Figure 14:
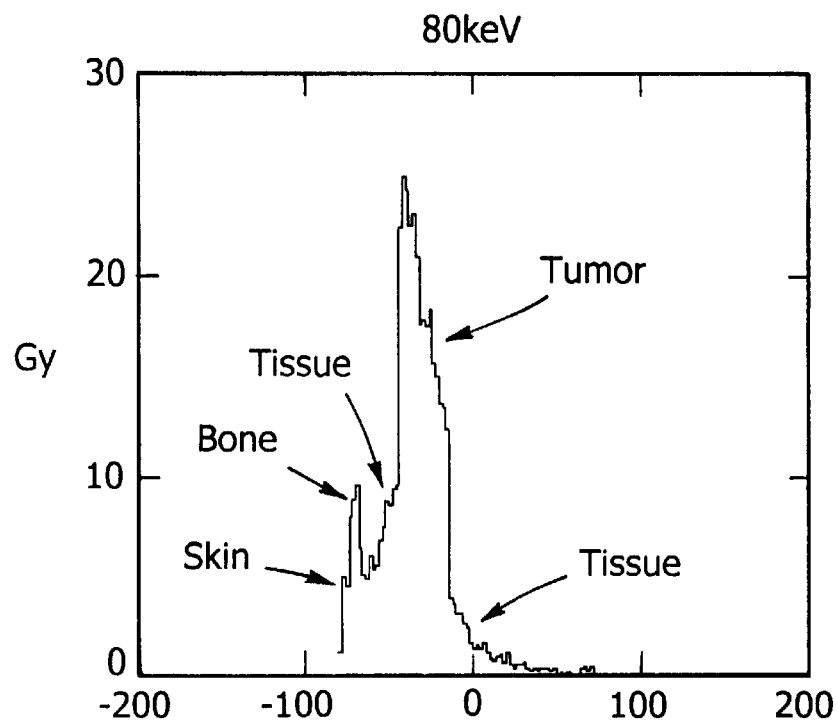
FIG. 14 illustrates the system of FIG. 13, but with an 80 keV beam.

When 2.4% iodine was delivered to the tumor 120, the situation became much more attractive. FIG. 12 illustrates a simple 57 keV beam (no arcs) passing through the head model 100 with iodine delivered to the tumor 120. The local dose leaps dramatically as it enters the tumor 120, creating a dose somewhat in excess of that of the skin layer 105, and approaching that to the bone layer 110. When arcs are added (FIG. 13), the dose distribution starts to approach the ideal. The dose inside the tumor 120 is much higher than everywhere outside the tumor 120 including the bone layer 110. This is needed to ensure that the tumor 120 is killed cleanly with a minimal dose to the healthy tissue 115. Finally, in FIG. 14, we illustrate the same arced geometry with an 80 keV beam. We find that the dose to the bone layer 110 is now minimized, but the tissue layer 115 just outside the tumor 120 receives a higher dose.

EXAMPLE 3

This example sets forth a preferred embodiment including radiosensitization with iodinated contrast agent and orthovoltage radiosurgery of malignant tumors. We treated three patients (on a compassionate-use basis) with iodinated contrast agent and photoelectric radiotherapy. The three patients had failed multiple conventional therapies and all had end stage disease (see Table I for the parameters of the patients treated by the method of the present invention).

TABLE I

Parameters of treated patients

| | Age | Gender | Pathology | Site | mtd | fx | kVp | mA |
|---|---|---|---|---|---|---|---|---|
| Patient 1 | 54 | Female | Melanoma | forearm, | 300 | 1 | 125 | 15 |
| | | | | back, | 500 | 1 | 125 | 15 |
| | | | | neck | 400 | 1 | 125 | 15 |
| Patient 2 | 65 | Male | NHL* | thigh 1 | 225 | 1 | 125 | 15 |
| | | | | thigh 2 | 200 | 1 | 125 | 10 |
| | | | | thigh 3, 4 | 150 | 1 | 125 | 10 |
| Patient 3 | 31 | Male | Lmyo** | abd, right | 225 | 1 | 125 | 10 |
| | | | | abd, left | 293 | 1 | 125 | 15 |

| | sec | ssd | diam | cvol | H | cer | toxic | resp |
|---|---|---|---|---|---|---|---|---|
| Patient 1 | 670 | 43 | 5 | 1 | 1700 | 5.3 | 0 | 1 |
| | 1200 | 43 | 5 | 1 | 0# | ?4 | 0 | 1 |
| | 1200 | 48 | 0 | 0.5 | 0# | ?4 | 0 | 1 |
| Patient 2 | 720 | 48 | 0 | 1 | 2019 | 6 | 0 | 2 |
| | 300 | 43 | 0 | 5 | 2100 | 6.25 | 0 | 2 |
| | 240 | 46 | 45/25 | 17 | 3071 | 8.7 | 0 | 1 |
| Patient 3 | 360 | 43 | 52 | 4.5 | 2000 | 6 | 0 | 1 |
| | 830 | 43 | 58 | 5 | 600 | 2.5 | 0 | 1 |

*Non-hodgkin's lymphoma
**Leiomyosarcoma
mtd- prescribed minimum tumor dose, the dose to the normal surrounding tissue
fx - number of fractions
kVp - peak kilovoltage
mA - milliamps
sec - treatment time in seconds
ssd - source-to-skin distance in cm
diam - diameter of lesion in mm
cvol - volume of contrast injected in ml
H - calculated Hounsfield units; (#) means concentration was not calculated
cer - enhancement ratio of radiation dose due to contrast
tox - toxicity (0 = none)
resp - response (0 = none, 1 = partial, 2 = complete)

Patient #1 was a 53-year-old woman with a 10-year history of metastatic melanoma. She had her first recurrence 5 years ago and had received multiple chemotherapies as well as gene therapy, hyperthermia, cisplatin, and melphalan infusion into her right lower extremity. She was treated with conventional radiotherapy to the entire right lower extremity because of massive tumor infiltration that had produced swelling and skin ulceration and made walking extremely uncomfortable. She received 30 Gy in 10 fractions and had a modest response. She had several exophytic lesions on her arms and back, which were bothersome. Two of these lesions were treated by conventional methods: the lesion on the back with orthovoltage alone (without response) and a left arm lesion with orthovoltage with contrast (with flattening of the lesion).

Under treatment by the methods of the present invention, the lesion on the left forearm was injected with iodinated contrast agent, approximately 1 ml per lesion, and then the injected site was imaged and the amount of iodine in the lesion was calibrated to determine the dose enhancement. The measurement of the maximum Hounsfield number H using a CT scanner led to a Hounsfield number H of 1700. Using the calibration equation de=1+0.0025 H, the dose enhancement de was calculated to be de=1+0.0025(1700)=5.3. She was then treated at 125 kVp and 15 mA for 670 seconds at a distance of 43 cm to deliver a dose of about 3 to about 5 Gy to the normal tissues and a dose to the lesion in which the dose was 5.3 times greater. That is, the minimal tumor dose was 300 cGy and the enhanced dose was therefore 300 cGy×5.3=1590 cGy. There were no adverse effects and the tumor flattened and turned gray. The patient did not undergo calibration of the contrast agent amount following the first treatment.

Patient #2 was a 64-year-old man, a quadriplegic for 43 years, who had a non-Hodgkin's lymphoma of the right lower leg. He had received conventional CHOP chemotherapy and 50 Gy of radiation initially. He received an additional 50 Gy to a field above the earlier field when he developed a recurrence. He developed another recurrence in the thigh and this was conventionally treated by radiotherapy with a course of 45 Gy in 15 fractions. A subsequent recurrence in this field was treated with conventional salvage chemotherapy. He relapsed again in this area and because he had received large doses of chemo/radiation therapy to the region and because of potential skin breakdown, he was not considered a candidate for further conventional local radiotherapy.

Under the methods of the present invention, the amount of contrast agent in the lesions was calibrated following injections of about 1 to about 17 ml of contrast agent into the tumors, and the dose enhancements were calculated as follows. For the first thigh lesion, the Hounsfield number H was measured to be 2019, and the dose enhancement de was therefore de=1+0.0025(2019)=6. Irradiation was performed at 125 kVp and 15 mA for 720 seconds at a distance of 48 cm. The minimum tumor dose thus being 225 cGy, the enhanced tumor dose for the first thigh tumor was therefore 6×225=1350 cGy. For the second thigh lesion, the Hounsfield number H was measured to be 2100, and the dose enhancement was calculated to be de=1+0.0025(2100)=6.25. Irradiation was performed at 125 kVp and 10 mA for 300 seconds at a distance of 43 cm. With the minimum tumor dose thus being 200 cGy, the enhanced tumor dose was therefore 6.25×200=1250 cGy. For the third thigh tumor, the Hounsfield number H was measured to be 3071, and the dose enhancement de was thus de=1+0.0025(3071)=8.7. Irradiation was performed at 125 kVp and 10 mA for 240 seconds at a distance of 46 cm. With a minimum tumor dose of 150 cGy, the dose enhancement to the tumor was therefore 150×8.7=1305 cGy. In all cases, there were no adverse reactions and the lesions responded dramatically. There was a complete disappearance of the first treated tumors by 6 months after treatment with minimal stigmata left on the skin; a large ulcerated tumor completely healed and left the overlying skin intact.

Patient #3 was a 31-year-old man, who presented with a small bowel tumor that was resected. The pathology indicated low-grade leiomyosarcoma. Five years later a 21-cm liver mass was discovered, and fine-needle aspiration confirmed a recurrent leiomyosarcoma. In addition, work-up demonstrated several lung nodules, a 10-cm left midquadrant mass, and near complete tumor invasion of his pelvis. A course of conventional MAID chemotherapy resulted in minimal changes. He was not considered a candidate for further conventional chemotherapy or radiotherapy. The massive tumor bulk was considered unresectable.

He was then treated by the methods of the present invention with orthovoltage x-rays and contrast agent. Injection of the tumors was performed by localizing the needle with CT guidance. Injections of approximately 5 ml of contrast agent produced a dose enhancement by a factor of about 2.5 times to about 3 times the minimal tumor dose of 293 Gy. That is, after injection of the contrast agent into the right abdominal tumor, the Hounsfield number H was 2000, and the dose enhancement de=1+0.0025(2000)=6. Irradiation was performed at 125 kVp and 10 mA for 360 seconds at a distance of 43 cm. The minimum tumor dose upon irradiation was therefore 225 cGy, giving a dose enhancement to the tumor of 225×6=1350 cGy. The Hounsfield number H for the left abdominal tumor was measured to be 600, and the dose enhancement de=1+0.0025(600)=2.5. Irradiation was performed at 125 kVp and 15 mA for 830 seconds at a distance of 43 cm. At a minimum tumor dose of 293 cGy, the enhanced dose to the tumor was therefore 293×2.5=733 cGy. The patient suffered no toxicity, and a follow-up scan at 2 weeks after irradiation showed that the diameter of the treated left abdominal lesion had shrunk from 5 cm to 3 cm, with the center of the tumor demonstrating radiographic evidence of necrosis. The patient underwent a two-stage resection of the tumors following the contrast agent-enhanced radiosurgery. The treated left abdominal lesion had turned fibrotic, and gross resection of the remaining masses was completed.

While the exemplary embodiments of the present invention are described herein with particularity, those having ordinary skill in the art will recognize various changes, modifications, additions, and applications other than those specifically described herein, and may adapt the preferred embodiment and methods without departing from the spirit of the invention. Other arrangements or embodiments, not precisely set forth, could be practiced under the teachings of the present invention and as set forth in the following claims.

We claim:

1. A method for treating tumors by radiosurgery with focused x-rays comprising the steps of:
    (a) delivering an amount of a contrast agent into a tumor;
    (b) calibrating the amount of said contrast agent within said tumor to determine x-ray dose enhancement;
    (c) repeating steps a and b until a desired amount of said contrast agent is delivered into said tumor to provide a desired amount of x-ray dose enhancement;
    (d) irradiating said tumor containing said desired amount of said contrast agent with focused x-rays,
said method resulting in an x-ray dose enhancement in said tumor of about 2:1 to about 10:1.

2. The method of claim 1 wherein said contrast agent is selected from the group consisting of iodine, gadolinium, and gold.

3. The method of claim 2 wherein said contrast agent is iodine.

4. The method of claim 1 wherein said step of delivering said contrast agent is performed by intravenous injection of said contrast agent.

5. The method of claim 1 wherein said step of delivering said contrast agent is performed by injecting said contrast agent directly into said tumor.

6. The method of claim 5 wherein said step of delivering said contrast agent injects said contrast agent into a surface portion of said tumor.

7. The method of claim 1 wherein said step of delivering said contrast agent is directed by ultrasonography.

8. The method of claim 1 wherein said step of calibrating the amount of said contrast agent to determine x-ray dose enhancement is performed with the equation de=1+1.3 p, where de means dose enhancement and p is the percentage of said contrast agent by weight in said tumor.

9. The method of claim 1 wherein said step of calibrating the amount of said contrast agent to determine x-ray dose enhancement is performed with a computed tomography scanner and further comprises the steps of:

(a) scanning said tumor with said computed tomography scanner:
    (b) determining a Hounsfield number H in said tumor with said computed tomography scanner;
    (c) using said Hounsfield number H to calculate the x-ray dose enhancement with the equation de=1+0.0025 H, where de equals dose enhancement.

10. The method of claim 1 wherein said focused x-rays have an energy of about 30 keV to about 150 keV.

11. The method of claim 10 wherein said focused x-rays have an energy of about 40 keV to about 80 keV.

12. A method for treating tumors by radiosurgery with focused x-rays, said method comprising the steps of:
    (a) injecting an amount of a contrast agent into a tumor;
    (b) calibrating the amount of said contrast agent within said tumor to determine x-ray dose enhancement with the equation de=1+1.3 p, where de means dose enhancement and p is the percentage of said contrast agent by weight in said tumor;
    (c) repeating steps a and b until a desired amount of said contrast agent is injected into said tumor to provide a desired amount of x-ray dose enhancement;
    (d) irradiating said tumor containing said desired amount of said contrast agent with focused x-rays having an energy of between about 40 keV and about 80 keV,
wherein said desired amount of said contrast agent results in an x-ray dose enhancement in said tumor of about 2:1 to about 10:1.

13. The method of claim 12 wherein said contrast agent is selected from the group consisting of iodine, gadolinium, and gold.

14. The method of claim 13 wherein said contrast agent is iodine.

15. The method of claim 12 wherein said step of injecting said contrast agent is directed by ultrasonography.

16. The method of claim 12 wherein said step of injecting said contrast agent injects said contrast agent into a surface portion of said tumor.

17. A method for treating tumors by radiosurgery with focused x-rays, said method comprising the steps of:
    (a) injecting an amount of a contrast agent into a tumor;
    (b) calibrating the amount of said contrast agent within said tumor to determine x-ray dose enhancement by the steps of:
        scanning said tumor injected with said contrast agent with a computed tomography scanner;
        determining a Hounsfield number H in said tumor with said computed tomography scanner;
        using said Hounsfield number H to calculate the dose enhancement with the equation de=1+0.0025 H;
    (c) repeating steps a and b until a desired amount of said contrast agent is injected into said tumor to provide a desired amount of x-ray dose enhancement;
    (d) irradiating said tumor containing said desired amount of said contrast agent with focused x-rays having an energy of between about 40 keV and about 80 keV,
wherein said desired amount of said contrast agent results in an x-ray dose enhancement in said tumor of about 2:1 to about 10:1.

18. The method of claim 17 wherein said contrast agent is selected from the group consisting of iodine, gadolinium, and gold.

19. The method of claim 18 wherein said contrast agent is iodine.

20. The method of claim 17 wherein said step of injecting said contrast agent is directed by ultrasonography.

21. The method of claim 17 wherein the step of injecting said contrast agent injects said contrast agent into a surface portion of said tumor.

22. A method for treating tumors by radiosurgery with focused x-rays, said method comprising the steps of:
(a) injecting an amount of a contrast agent into a surface portion of a tumor;
(b) calibrating the amount of said contrast agent within said surface portion of said tumor to determine x-ray dose enhancement with the equation de=1+1.3 p, where de means dose enhancement and p is the percentage of said contrast agent by weight in said surface portion of said tumor;
(c) repeating steps a and b until a desired amount of said contrast agent is injected into said surface portion of said tumor to provide a desired amount of x-ray dose enhancement;
(d) irradiating said tumor containing said desired amount of said contrast agent with focused x-rays having an energy of between about 40 keV and about 80 keV,
wherein said desired amount of said contrast agent results in an x-ray dose enhancement in said surface portion of said tumor of about 2:1 to about 10:1.

23. The method of claim 22 wherein said contrast agent is selected from the group consisting of iodine, gadolinium, and gold.

24. The method of claim 23 wherein said contrast agent is iodine.

25. The method of claim 22 wherein said step of injecting said contrast agent is directed by ultrasonography.

26. A method for treating tumors by radiosurgery with focused x-rays, said method comprising the steps of:
(a) injecting an amount of a contrast agent into a surface portion of a tumor;
(b) calibrating the amount of said contrast agent within said surface portion of said tumor to determine x-ray dose enhancement by the steps of:
scanning said surface portion of said tumor injected with said contrast agent with a computed tomography scanner;
determining a Hounsfield number H in said surface portion of said tumor with said computed tomography scanner;
using said Hounsfield number H to calculate the dose enhancement with the equation de=1+0.0025 H;
(c) repeating steps a and b until a desired amount of said contrast agent is injected into said surface portion of said tumor to provide a desired amount of x-ray dose enhancement;
(d) irradiating said tumor containing said desired amount of said contrast agent with focused x-rays having an energy of between about 40 keV and about 80 keV,
wherein said desired amount of said contrast agent results in an x-ray dose enhancement in said surface portion of said tumor of about 2:1 to about 10:1.

27. The method of claim 26 wherein said contrast agent is selected from the group consisting of iodine, gadolinium, and gold.

28. The method of claim 27 wherein said contrast agent is iodine.

29. The method of claim 26 wherein said step of injecting said contrast agent is directed by ultrasonography.

30. A method for treating tumors by radiosurgery with focused x-rays, said method comprising the steps of:
(a) injecting an amount of a contrast agent into a tumor, wherein said step of injecting said contrast agent is directed by ultrasonography;
(b) calibrating the amount of said contrast agent within said tumor to determine x-ray dose enhancement with the equation de=1+1.3 p, where de means dose enhancement and p is the percentage of said contrast agent by weight in said tumor;
(c) repeating steps a and b until a desired amount of said contrast agent is injected into said tumor to provide a desired amount of x-ray dose enhancement;
(d) irradiating said tumor containing said desired amount of said contrast agent with focused x-rays having an energy of between about 40 keV and about 80 keV,
wherein said desired amount of said contrast agent results in an x-ray dose enhancement in said tumor of about 2:1 to about 10:1.

31. The method of claim 30 wherein said contrast agent is selected from the group consisting of iodine, gadolinium, and gold.

32. The method of claim 31 wherein said contrast agent is iodine.

33. A method for treating tumors by radiosurgery with focused x-rays, said method comprising the steps of:
(a) injecting an amount of a contrast agent into a tumor, wherein said step of injecting said contrast agent is directed by ultrasonography;
(b) calibrating the amount of said contrast agent within said tumor to determine x-ray dose enhancement by the steps of:
scanning said tumor injected with said contrast agent with a computed tomography scanner;
determining a Hounsfield number H in said tumor with said computed tomography scanner;
using said Hounsfield number H to calculate the dose enhancement with the equation de=1+0.0025 H;
(c) repeating steps a and b until a desired amount of said contrast agent is injected into said tumor to provide a desired amount of x-ray dose enhancement;
(d) irradiating said tumor containing said desired amount of said contrast agent with focused x-rays having an energy of between about 40 keV and about 80 keV,
wherein said desired amount of said contrast agent results in an x-ray dose enhancement in said tumor of about 2:1 to about 10:1.

34. The method of claim 33 wherein said contrast agent is selected from the group consisting of iodine, gadolinium, and gold.

35. The method of claim 34 wherein said contrast agent is iodine.

* * * * *